(12) United States Patent
Nagai et al.

(10) Patent No.: US 6,388,022 B1
(45) Date of Patent: May 14, 2002

(54) LINKER BINDING CARRIERS FOR ORGANIC SYNTHESIS, THEIR PRODUCTION AND USE

(75) Inventors: Katsunori Nagai; Tetsuo Miwa, both of Hyogo (JP)

(73) Assignee: Takeda Chemical Industires, Ltd., Osaka (JP)

( * ) Notice: Subject to any disclaimer, the term of this patent is extended or adjusted under 35 U.S.C. 154(b) by 0 days.

(21) Appl. No.: 09/385,953

(22) Filed: Aug. 30, 1999

(30) Foreign Application Priority Data

Sep. 10, 1998 (JP) .......................................... 10-257264

(51) Int. Cl.$^7$ ..................... C07C 309/73; C07C 309/75; C07C 309/76; C07C 309/86; C07C 309/87
(52) U.S. Cl. ........................ 525/421; 544/398; 544/399; 546/236; 546/237; 558/46; 558/52; 562/828; 562/831
(58) Field of Search ................................ 562/828, 831; 558/46, 52; 546/236, 237; 544/398, 399; 5258/421

(56) References Cited

U.S. PATENT DOCUMENTS 4,370,410 A  1/1983 Iijima et al. ................. 430/505

FOREIGN PATENT DOCUMENTS

WO  WO 98/29386  7/1998

OTHER PUBLICATIONS

E. Baxter et al., "Arylsulfonate Esters in Solid Phase Organic Synthesis. II. . . . " *Tetrahedron Letters* 39(1998) 979–982.

J. Rueter et al., "Arylsulfonate Esters in Solid Phase Organic Synthesis. I. . . . " *Tetrahedron Letters* 39(1998) 975–978.

S. Jin et al., "Reductive Cleavage of Resin Bound Arylsulfonates" *Tetrahedron Letters* 39(1998) 3651–3654.

K. Kamahori et al., "Synthesis of Polymer–Supported Chiral . . . " *Tetrahedron: Asymmetry* vol. 6, No. 10, (1995) pp. 2547–2555.

H. Kamogawa et al., "Conversions of Carbonyl Compounds . . . " *Bull. Chem. Soc. Jpn.*, 56 No. 3, (1983) 762–765.

Boyle et al., Chemical Abstracts, vol. 126:225210, 1997.

Hirst et al., Chemical Abstracts, vol. 123:28397, 1995.

Andreea et al., Chemical Abstracts, vol. 115:250648, 1991.

Hovius et al., Chemicla Abstracts, vol. 99:139451, 1983.

*Primary Examiner*—Richard L. Raymond
(74) *Attorney, Agent, or Firm*—Mark Chao; Elaine M. Ramesh

(57) ABSTRACT

The present invention provides a linker binding carrier for organic synthesis represented by the formula:

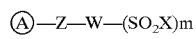

wherein

Ⓐ is a carrier, X is a leaving group, Y is a bond or spacer, Z is a bivalent group, when Z is a bivalent electron attractive group, W is an aromatic ring which may be substituted and when Z is a bivalent non-electron attractive group, W is an aromatic ring which is substituted by an electron attractive group and may be further substituted and m is 1 or 2, or a salt thereof, which is useful for synthesizing a novel organic compound.

19 Claims, No Drawings

LINKER BINDING CARRIERS FOR ORGANIC SYNTHESIS, THEIR PRODUCTION AND USE

TECHNICAL FIELD

The present invention relates to novel carriers extremely useful in synthesis of organic compounds (particularly in the field of combinatorial chemistry), as well as the production method and uses thereof.

BACKGROUND ART

In the field of combinatorial chemistry, compounds to be synthesized are linked via covalent bonds to carriers (e.g. resin, etc.) for organic synthesis on the carriers. For this linkage mode, various chemical structures are known and described in detail for example by G. Jung et al. (Angew. Chem. Int. Ed. Engl., Vol. 35, p. 17 (1996)). This covalent bond moiety for linking a synthetic compound to a carrier is usually called a linker in this field.

In the case of the conventional linkage mode, functional groups derived from the chemical structure of the linker moiety will usually remain in a product upon cleaving the synthetic compound off from the carriers. Such known functional groups include e.g. carboxyl groups, their derivatives, hydroxy groups, amino groups, etc. These functional groups are not necessarily required for exhibiting the action of a functional substance in the synthetic compound, or the presence of these functional groups interferes often with the action of the functional substance, and these remaining functional groups constitute one major factor limiting the type of compounds which can be synthesized by a synthesis method using carriers.

However, a method of permitting no functional group derived from a linker to remain on a product, that is, a synthesis method of using a traceless linker, has been recently reported. For example, traceless linkers making use of the binding properties of aryl-silane are reported by A. Ellman et al. (J. Org. Chem., Vol. 60, p. 6006 (1995)) and D. F. Veber et al. (J. Am. Chem. Soc., Vol. 117, p. 11999 (1995)). In any of these methods, however, formation of aryl-silane bonds requires lithiation of aryl groups with a strong base, so in this step, functional groups unstable to the base cannot be present at the side of the aryl group. Further, there is also the case where the aryl-silane bonds are hardly cleaved owing to the properties of substituent groups on the aryl group. For this reason, the type of compounds to which the aryl-silane-type traceless linker can be applied has been limited.

Meanwhile, D. J. Wustrow et al. (Tetrahedron Lett., Vol. 39, p. 3651 (1998)) have reported a method of reacting a phenol derivative bound to sulfonate resin with a palladium catalyst and formic acid salt to obtain its corresponding benzene derivative. However, this method of using the linker-bound carrier derived from the sulfonate type ion-exchange resin is applicable only to synthesis of benzene derivatives substituted with electron attractive groups such as carboxyl group, carbamoyl group etc., so this is not a synthesis method that is universally applicable to the preparation of a wide variety of aromatics.

The present invention provides linker-bound carriers for organic synthesis, which carry a novel traceless linker universally applicable to synthesis of various synthetic compounds resulting desired synthetic compounds, free of any functional group derived from the linker, as well as a process for producing the same and uses thereof.

As a result of their studies, the present inventors first synthesized carriers to which linkers represented by the formula:

Y—Z—W—(SO$_2$X)m wherein each symbol has the same meaning as defined below, have been bound, and they unexpectedly found that these carriers, owing to the special chemical structure of their linker moiety, achieved such excellent characteristics that various compounds, particularly synthetic compounds having aromatic hydroxy groups as substrate, are easily carried onto the carriers, the synthetic compounds can be carried on the carriers stably even under various organic synthesis reaction conditions, the desired synthetic compounds can be easily cleaved therefrom, and the resulting synthetic compounds do not have any functional group derived from the linker moiety, and on the basis of these findings, the present invention was completed.

DISCLOSURE OF INVENTION

The present invention provides:

(1) A linker binding carrier for organic synthesis represented by the formula:

   (I)

wherein
Ⓐ is a carrier, X is a leaving group, Y is a bond or spacer, Z is a bivalent group, when Z is a bivalent electron attractive group, W is an aromatic ring which may be substituted and when Z is a bivalent non-electron attractive group, W is an aromatic ring which is substituted by an electron attractive group and may be further substituted and m is 1 or 2, or a salt thereof, (2) A linker binding carrier for organic synthesis or a salt thereof as defined in (1), wherein X is (i) a halogen atom or (ii) a sulfonyloxy group which may be substituted by alkyl or aryl, (3) A linker binding carrier for organic synthesis or a salt thereof as defined in (1), wherein X is (i) a halogen atom or (ii) a sulfonyloxy group which may be substituted by $C_{1-6}$ alkyl or $C_{6-14}$ aryl, (4) A linker binding carrier for organic synthesis or a salt thereof as defined in (1), wherein X is a halogen atom, (5) A linker binding carrier for organic synthesis or a salt thereof as defined in (1), wherein X is a chlorine atom, (6) A linker binding carrier for organic synthesis or a salt thereof as defined in (1), wherein the spacer represented by Y is an optionally substituted chained bivalent group composed of 1 to 20 atoms selected from the group consisting of carbon, nitrogen, hydrogen, oxygen and sulfur, (7) A linker binding carrier for organic synthesis or a salt thereof as defined in (1), wherein the spacer represented by Y is

   (i)

   (ii)

   (iii)

   (iv)

   (v)

   (vi)

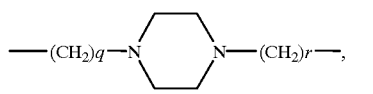
(vii)

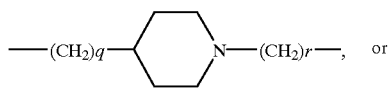
or
(viii)

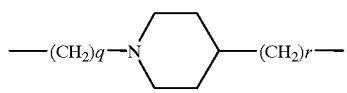
(ix)

wherein p is an integer of 1 to 6, q is an integer of 1 to 3, r is an integer of 1 to 3 and $R^1$ is a $C_{1-6}$ alkyl group, (8) A linker binding carrier for organic synthesis or a salt thereof as defined in (1), wherein the spacer represented by Y is

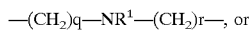
(i)

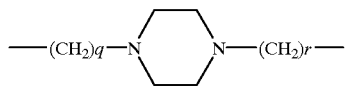
(ii)

wherein q is an integer of 1 to 3, r is an integer of 1 to 3 and $R^1$ is a $C_{1-6}$ alkyl group, (9) A linker binding carrier for organic synthesis or a salt thereof as defined in (1), wherein Y is a bond, —CH$_2$NH— or a group represented by

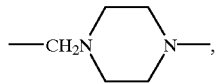

(10) A linker binding carrier for organic synthesis or a salt thereof as defined in (1), wherein the bivalent electron attractive group represented by Z is a substituent group wherein the Hammet's substituent constant σ has a positive value,

(11) A linker binding carrier for organic synthesis or a salt thereof as defined in (1), wherein the bivalent electron attractive group represented by Z is a carbonyl group, a thiocarbonyl group, a sulfonyl group, a sulfinyl group, a carbamoyl group, a thiocarbamoyl group, a halogeno-methene group or a halogeno-ethene group,

(12) A linker binding carrier for organic synthesis or a salt thereof as defined in (1), wherein the bivalent electron attractive group represented by Z is a carbonyl group, a thiocarbonyl group, a sulfonyl group or a sulfinyl group,

(13) A linker binding carrier for organic synthesis or a salt thereof as defined in (1), wherein the bivalent electron attractive group represented by Z is a carbonyl group or a sulfonyl group,

(14) A linker binding carrier for organic synthesis or a salt thereof as defined in (1), wherein the bivalent non-electron attractive group represented by Z is a $C_{1-6}$ alkylene group, $C_{2-6}$ alkenylene group or $C_{2-6}$ alkynylene group, which is substituted by hydroxy, amino, carboxyl, nitro, (mono- or di-$C_{1-6}$ alkyl)amino, $C_{1-6}$ alkoxy, ($C_{1-6}$ alkyl)carbonyloxy or a halogen atom

(15) A linker binding carrier for organic synthesis or a salt thereof as defined in (1), wherein the bivalent non-electron attractive group represented by Z is a methylene group or an ethylene group,

(16) A linker binding carrier for organic synthesis or a salt thereof as defined in (1), wherein Y is a bond and Z is a sulfonyl group or a carbonyl group,

(17) A linker binding carrier for organic synthesis or a salt thereof as defined in (1), wherein Y is —CH$_2$NH— or a group represented by

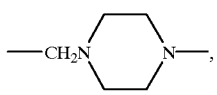

Z is a sulfonyl group or a carbonyl group,

(18) A linker binding carrier for organic synthesis or a salt thereof as defined in (1), wherein the aromatic ring is (i) a $C_{6-14}$ aromatic cyclic hydrocarbon or (ii) an aromatic heterocycle containing 1 to 4 hetero atoms selected from the group consisting of an oxygen atom, a sulfur atom and a nitrogen atom or its condensed ring, and the $C_{6-14}$ aromatic cyclic hydrocarbon and the aromatic heterocycle or its condensed ring may be substituted by (i) a halogen atom, (ii) a $C_{1-6}$ alkyl group which may be substituted by 1 to 3 halogen, (iii) a $C_{1-6}$ alkoxy group which may be substituted by 1 to 3 halogen, (iv) a $C_{1-6}$ alkylthio group which may be substituted by 1 to 3 halogen and (v) a hydroxy group,

(19) A linker binding carrier for organic synthesis or a salt thereof as defined in (1), wherein the $C_{6-14}$ aromatic cyclic hydrocarbon is a benzene ring,

(20) A linker binding carrier for organic synthesis or a salt thereof as defined in (1), wherein the aromatic heterocycle or its condensed ring is furan, thiophene, pyrrole, oxazole, isoxazole, thiazole, isothiazole, imidazole, pyrazole, pyridine, pyridazine, pyrimidine, pyrazine, triazine, benzofuran, isobenzofuran, benzothiophene, indole, isoindole, 1H-indazole, benzimidazole, benzoxazole, 1,2-benzisoxazole, benzothiazole, benzopyrane, quinoline, isoquinoline, cinnoline, quinazoline, quinoxaline, phthalazine, naphthyridine, purine, pteridine, carbazole, α-carboline, β-carboline, γ-carboline, acridine, phenoxazine, phenothiazine, phenazine, phenoxathiin, thianthrene, phenanthridine or phenanthroline,

(21) A linker binding carrier for organic synthesis or a salt thereof as defined in (1), wherein the electron attractive group on the ring represented by W is a halogen atom, a halogeno-$C_{1-6}$ alkyl group, a halogeno-$C_{6-14}$ aryl group, a $C_{1-6}$ alkylsulfonyl group, a $C_{6-14}$ aryl sulfonyl group, a $C_{1-6}$ alkylsulfamoyl group, a $C_{6-14}$ arylsulfamoyl group, a $C_{1-6}$ alkylsulfinyl group, a $C_{6-14}$ arylsulfinyl group, a $C_{1-6}$ alkoxycarbonyl group, a $C_{6-14}$ aryloxy-carbonyl group, a carbamoyl group, a thiocarbamoyl group, a carboxyl group, an acyl group, a formyl group, a nitro group or a cyano group,

(22) A linker binding carrier for organic synthesis or a salt thereof as defined in (1), wherein the carrier represented by

is a carrier represented by

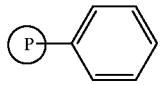

wherein

is a polystyrene carrier,

(23) A linker binding carrier for organic synthesis or a salt thereof as defined in (22), wherein the polystyrene carrier is a co-polymer comprising a styrene and 0 to 5 mol % of divinylbenzene thereto,

(24) A linker binding carrier for organic synthesis or a salt thereof as defined in (1), which is represented by the formula:

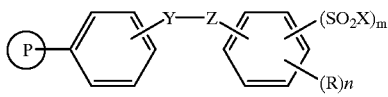

(III)

wherein

is a polystyrene carrier, R is a lower alkyl group, n is an integer of 0 to 4 and when n is not less than 2, R may be same or different, the sum of m and n is not more than 5, and other symbols are as defined in (1),

(25) A linker binding carrier for organic synthesis or a salt thereof as defined in (24), wherein X is a chlorine atom,

(26) A linker binding carrier for organic synthesis or a salt thereof as defined in (24), wherein Y is —$CH_2NH$— or a group represented by

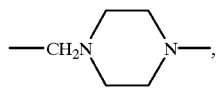

Z is a sulfonyl or carbonyl group and n is 0,

(27) A linker binding carrier for organic synthesis or a salt thereof as defined in (1), wherein the carrier represented by

is a carrier represented by

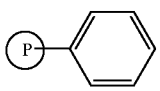

(II)

wherein

is a polystyrene carrier, X is a halogen atom, Y is a bond, —$CH_2NH$— or a group represented by

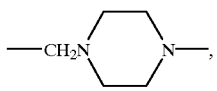

Z is a sulfonyl group or a carbonyl group, W is a benzene ring, m is 1 or 2,

(28) A method for producing a linker binding carrier for organic synthesis represented by the formula:

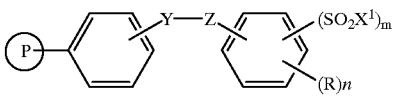

(V)

wherein $X^1$ is (i) a halogen atom or (ii) a sulfonyloxy group substituted by lower alkyl or aromatic ring, and other symbols are as defined in (24), or a salt thereof which comprises reacting (i) a halogenating reagent or (ii) a reagent for activating sulfonic acid with a compound represented by the formula:

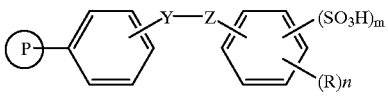

(IV)

wherein the symbols are as defined above,

(29) The method as defined in (28), wherein the halogenating reagent is a sulfuryl halide,

(30) A method for producing a linker binding carrier for organic synthesis represented by the formula:

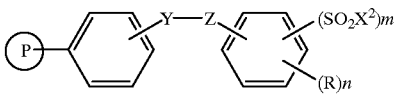

(VII)

wherein $X^2$ is a halogen atom and other symbols are as defined in (24), or a salt thereof which comprises reacting a compound represented by the formula:

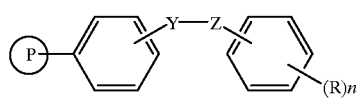
(VI)

wherein the symbols are as defined in (24) with a halogeno-sulfonic acid,

(31) A method for producing a linker binding carrier for organic synthesis represented by the formula:

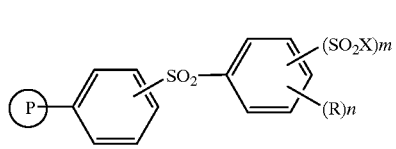
(IX)

wherein the symbols are as defined in (24), which comprises reacting a carrier represented by

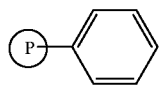
(II)

wherein

is as defined above with a compound represented by the formula:

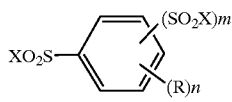
(VIII)

wherein the symbols are as defined above,

(32) A method for producing a linker binding carrier for organic synthesis represented by the formula:

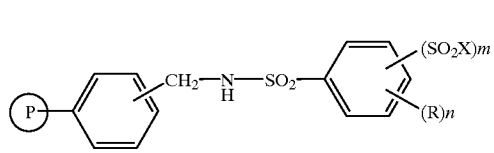
(XI)

wherein the symbols are as defined in (24) or a salt thereof, which comprises reacting a compound represented by the formula:

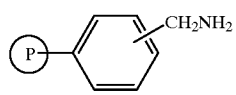
(X)

wherein the symbols are as defined above, or a salt thereof with a compound represented by the formula:

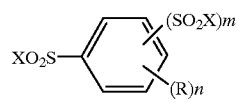
(VIII)

wherein the symbols are as defined above, or a salt thereof,

(33) A method for producing a linker binding carrier for organic synthesis represented by the formula:

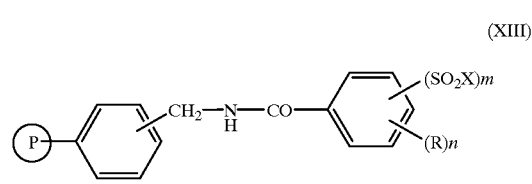
(XIII)

wherein the symbols are as defined in (24) or a salt thereof, which comprises reacting a compound represented by the formula:

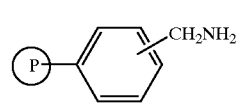
(X)

wherein the symbol is as defined above, or a salt thereof with a compound represented by the formula:

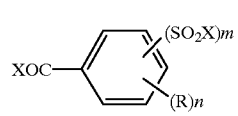
(XII)

wherein each symbols are as defined above, or a salt thereof,

(34) A method for producing a linker binding carrier for organic synthesis represented by the formula:

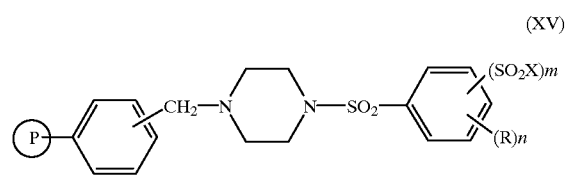
(XV)

wherein the symbols are as defined in (24) or a salt thereof, which comprises reacting a compound represented by the formula:

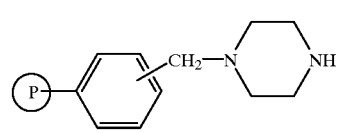
(XIV)

wherein the symbol is as defined above, or a salt thereof with a compound represented by the formula:

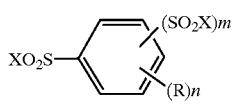
(VIII)

wherein the symbols are as defined above, or a salt thereof,

(35) A method for producing a linker binding carrier for organic synthesis represented by the formula:

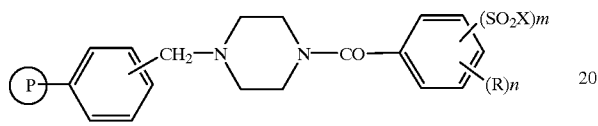
(XVI)

wherein the symbols are as defined in (24) or a salt thereof, which comprises reacting a compound represented by the formula:

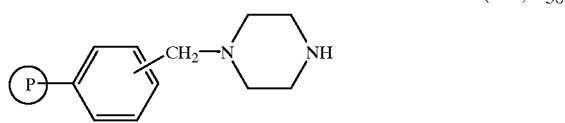
(XIV)

wherein the symbol is as defined above, or a salt thereof with a compound represented by the formula:

(XII)

wherein the symbols are as defined above, or a salt thereof,

(36) A method for producing a linker binding carrier for organic synthesis represented by the formula:

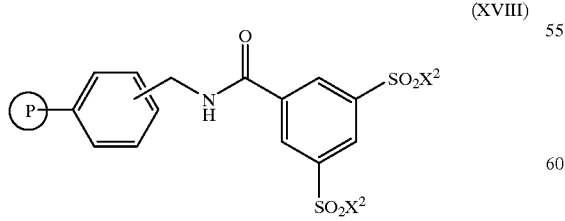
(XVIII)

wherein $X^2$ is a halogen atom and other symbols are as defined in (24), or a salt thereof, which comprises reacting a compound represented by the formula:

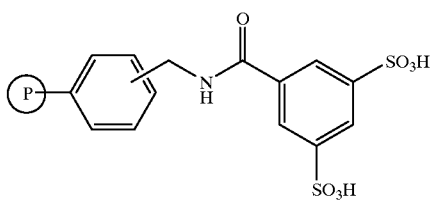
(XVII)

wherein the symbol is as defined above with a sulfuryl halide,

(37) A method for synthesizing an organic compound which comprises using a linker binding carrier for organic synthesis or a salt thereof as defined in (1),

(38) The method as defined in (37) which is a method for synthesizing a compound represented by the formula:

Ar'—H  (XXII)

wherein Ar' is an aromatic ring which may be substituted, or a salt thereof, which comprises
(i) reacting a compound represented by the formula:

Ar—OH  (XIX)

wherein Ar is an aromatic ring which may be substituted, or a salt thereof, with a linker binding carrier for organic synthesis represented by the formula:

(A)—Y—Z—W—(SO₂X)m  (I)

wherein the symbols are as defined in (1), or a salt thereof in the basic condition, and
(ii) if necessary, introducing substituents on Ar or/and converting the substituents on Ar into other substituents of the obtained compound represented by the formula:

(A)—Y—Z—W—(SO₂OAr)m  (XX)

wherein the symbols are as defined above, and
(iii) subjecting the obtained compound represented by the formula:

(A)—Y—Z—W—(SO₂Ar')m  (XXI)

wherein the symbols are as defined above or a salt thereof to a reducing reaction,

(39) The method as defined in (38) which comprises subjecting a reducing reaction by using a salt of formic acid or trialkylsilane in presence of palladium phosphine complex,

(40) The method as defined in (38) wherein the aromatic ring represented by Ar and Ar' is a benzene ring,

(41) A compound represented by the formula:

(A)—Y—Z—W—(SO₂OAr')m  (XXI)

wherein Ar' is an aromatic ring which may be substituted and other symbols are as defined in (1), or a salt thereof,

(42) A method for synthesizing a compound represented by the formula:

Ar'—H　(XXII)

wherein Ar' is an aromatic ring which may be substituted, or a salt thereof, which comprises subjecting a compound represented by the formula:

(A)—Y—Z—W—(SO₂OAr')m　(XXI)

wherein Ar' is an aromatic ring which may be substituted and other symbols are as defined in (1), or a salt thereof to a reducing reaction,

(43) A novel organic compound obtainable by using the linker binding carrier for organic synthesis or a salt thereof as defined in (1), and

(44) A method of using the linker binding carrier for organic synthesis or a salt thereof as defined in (1) for synthesizing a novel organic compound.

DETAILED DESCRIPTION

The carriers represented by the formula:

(A)

may be various carriers used in the field of organic synthetic chemistry, inter alia combinatorial chemistry, for example, synthetic carriers generally used for peptide synthesis, silica gel etc., and preferably polystyrene available as commercial preparations. In particular, carriers consisting of polystyrene in the form of copolymers between styrene and divinyl benzene wherein the amount of the latter is about 0 to about 5 mole-% relative to the former are preferable for enhancing insolubility and stability in organic solvent, and those in the form of copolymers with about 1 to about 2 mole-% divinyl benzene are more preferable.

Preferable carriers may be granular ones with a diameter of e.g. about 30 to about 1500 μm.

Preferable examples of carriers consisting of polystyrene as (A)

may be compounds represented by the formula (II):

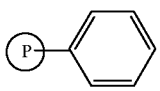

(II)

where the phenyl group in the formula (II) is derived from a styrene group in polystyrene, and one or more phenyl groups may be present in the formula (II), but for the sake of convenience, only one phenyl group is shown as a typical example in the present specification. Accordingly, the polystyrene carrier represented by the formula:

(P) in formula (II) means the remainder of polystyrene resin from which at least one phenyl group has been removed.

Further, the carriers are not particularly limited in form, and carriers in the form of resin, gel, sol etc. in addition to granular carriers are preferably used.

Examples of the leaving groups represented by X and X¹ are leaving groups generally used in the field of organic synthesis chemistry. Specifically, examples of leaving groups are those described in Comprehensive Organic Synthesis, Vol. 6, 5.1 (A. Krebs et al., Pergamon Press, Oxford, 1991) and so on, and more preferably (i) a halogen group (e.g., chloro, bromo, iodo), (ii) a sulfonyloxy group substituted by alkyl such as $C_{1-6}$ alkyl (e.g., methyl, ethyl, propyl, isopropyl, etc.) or aryl such as $C_{6-10}$ aryl (e.g., phenyl, tolyl, etc.) and so on, for example, a $C_{6-10}$ arylsulfonyloxy group (e.g., benzenesulfonyloxy, p-tolylsulfonyloxy) and a $C_{1-4}$ alkylsulfonyloxy group (e.g., methanesulfonyloxy).

Examples of halogen atom represented by $X^2$ are fluorine, chlorine, bromine, iodine, etc., preferably chlorine and bromine.

Examples of the spacer represented by Y are an optionally substituted bivalent group and so on. The optionally substituted bivalent group may be a straight-chained bivalent group composed of 1 to 20 atoms selected from the group consisting of carbon, nitrogen, hydrogen, oxygen, sulfur, etc., and is not cleaved under reaction conditions in each reaction procedures, more preferable examples of the bivalent group are those including carbon and nitrogen atoms.

Specific examples of the spacer are

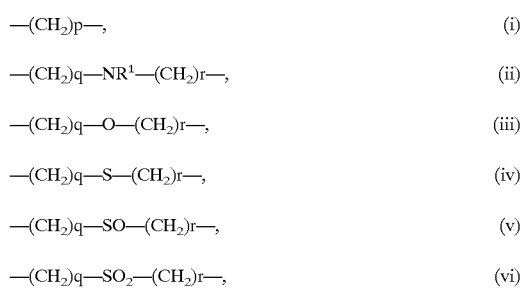

—(CH₂)p—,　(i)

—(CH₂)q—NR¹—(CH₂)r—,　(ii)

—(CH₂)q—O—(CH₂)r—,　(iii)

—(CH₂)q—S—(CH₂)r—,　(iv)

—(CH₂)q—SO—(CH₂)r—,　(v)

—(CH₂)q—SO₂—(CH₂)r—,　(vi)

etc., and a group represented by the formula:

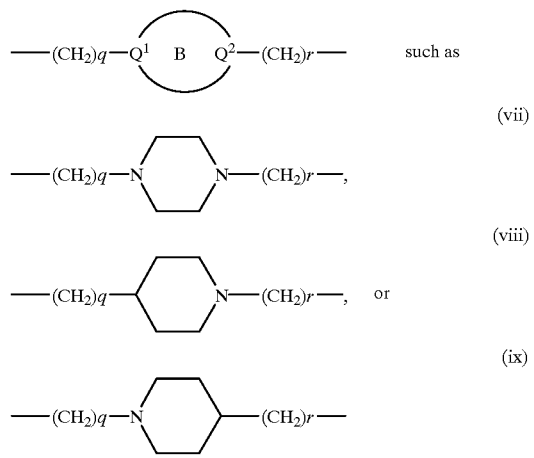

—(CH₂)q—Q¹　B　Q²—(CH₂)r—　such as (vii)

—(CH₂)q—N⟨　⟩N—(CH₂)r—, (viii)

—(CH₂)q—⟨　⟩N—(CH₂)r—,　or (ix)

—(CH₂)q—N⟨　⟩—(CH₂)r— wherein P is an integer of 1 to 6, q is an integer of 1 to 3, r is an integer of 1 to 3, $R^1$ is a $C_{1-6}$ alkyl group, one of $Q^1$ and $Q^2$ is a nitrogen atom and the other is a nitrogen atom or a carbon atom, ring B form a 5- to 7-membered ring together with $Q^1$ and $Q^2$. Preferable examples of the spacer are

—(CH₂)q—NR¹—(CH₂)r—,　(i)

 (ii)

wherein q is an integer of 1 to 3, r is an integer of 1 to 3 and $R^1$ is a $C_{1-6}$ alkyl group, etc., and more preferable examples are —$CH_2NH$—, a group represented by

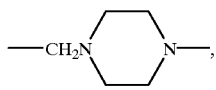, etc.

The bivalent group represented by Z is not limited so long as the purpose of the present invention is achieved, and it may be a bivalent electron attractive group or non-electron attractive group.

Here, the divalent electron attractive group means atoms attracting electrons stronger toward it from the side of bound atom than a hydrogen atom does, and specifically this group is a substituent group wherein the Hammet's substituent constant σ (L. P. Hammet, Physical Organic Chemistry, 2nd ed., McGrow-Hill, New York, 1970) has a positive value.

Examples of the bivalent electron attractive group are a carbonyl group, a thiocarbonyl group, a sulfonyl group, a sulfinyl group, a carbamoyl group, a thiocarbamoyl group, a halogeno-methene group, a halogeno-ethene group and so on, preferably a carbonyl group, a thiocarbonyl group, a sulfonyl group, a sulfinyl group and so on.

Examples of the bivalent non-electron attractive group are a $C_{1-6}$ alkylene group such as methylene, ethylene, etc., a $C_{2-6}$ alkenylene group such as vinylene, etc., a $C_{2-6}$ alkynylene group such as ethynylene, etc., and so on, and preferably a $C_{1-6}$ alkylene group such as methylene, ethylene, etc. The $C_{1-6}$ alkylene group, a $C_{2-6}$ alkenylene group and $C_{2-6}$ alkynylene may be substituted by 1 to 3 substituents at possible positions, respectively.

Examples of the substituents of the $C_{1-6}$ alkylene group, a $C_{2-6}$ alkenylene group and $C_{2-6}$ alkynylene are hydroxy, amino, carboxyl, nitro, (mono- or di-$C_{1-6}$ alkyl)amino, $C_{1-6}$ alkoxy, ($C_{1-6}$ alkyl)carbonyloxy, a halogen atom and so on.

When Z is an electron attractive group, W is an aromatic ring which may be substituted. The substituents may substitute on the possible positions on the aromatic ring. Examples of the substituents are (i) a halogen atom (e.g. chlorine, bromine, fluorine), (ii) a $C_{1-6}$ alkyl group (e.g. methyl, ethyl, etc.) which may be substituted by 1 to 3 halogen (e.g. chlorine, bromine, fluorine), (iii) a $C_{1-6}$ alkoxy group (e.g. methoxy, ethoxy, etc.) which may be substituted by 1 to 3 halogen (e.g. chlorine, bromine, fluorine), (iv) a $C_{1-6}$ alkylthio group (e.g. methylthio, ethylthio, etc.) which may be substituted by 1 to 3 halogen (e.g. chloroine, bromine, fluorine), (v) a hydroxy group and so on. The number of the substituents is 1 to 2. When the number of the substituents is 2, the substituents may be same or different.

Examples of the aromatic ring are an aromatic cyclic hydrocarbon or an aromatic heterocycle, preferably an aromatic cyclic hydrocarbon.

Examples of the aromatic ring are a monocyclic- or condensed polycyclic-aromatic hydrocarbone, preferably $C_{6-14}$ aromatic hydrocarbone such as benzene, naphthalene, anthracene, phenanthrene, acenaphthalene, etc., more preferably benzene.

Examples of the aromatic heterocycle are an aromatic heterocycle containing at least one hetero atom (preferably 1 to 4, more preferably 1 or 2) and 1 to 3 kinds (preferably 1 or 2 kinds) of hetero atoms selected from the group consisting of an oxygen atom, a sulfur atom, a nitrogen atom and so on as atoms composing the ring.

Examples of the aromatic heterocycle are (i) 5- or 6-membered aromatic monocyclic hetero ring such as furan, thiophene, pyrrole, oxazole, isoxazole, thiazole, isothiazole, imidazole, pyrazole, pyridine, pyridazine, pyrimidine, pyrazine, triazine, or (ii) 8- to 14-membered aromatic condensed heterocycle (preferably, a condensed heterocycle of the above-mentioned 5- or 6-membered aromatic monocyclic hetero ring and benzene ring, or a condensed heterocycle of same or different two of the above-mentioned 5- or 6-membered aromatic monocyclic hetero ring) such as benzofuran, isobenzofuran, benzothiophene, indole, isoindole, 1H-indazole, benzimidazole, benzoxazole, 1,2-benzoisoxazole, benzothiazole, benzopyrane, quinoline, isoquinoline, cinnoline, quinazoline, quinoxaline, phthalazine, naphthyridine, purine, pteridine, carbazole, α-carboline, β-carboline, γ-carboline, acridine, phenoxazine, phenothiazine, phenazine, phenoxathiin, thianthrene, phenanthridine, phenanthroline, and so on.

When Z is a bivalent non-electron attractive group, W is an aromatic ring which is substituted by an electron attractive group and may be further substituted.

Examples of the electron attractive group are a halogen atom, a halogeno-alkyl group (preferably, an alkyl group substituted by halogen at 1-position carbon atom, more preferably perhalogeno-alkyl group), a halogeno-aryl group, an alkylsulfonyl group, an aryl sulfonyl group, an alkylsulfamoyl group, an arylsulfamoyl group, an alkylsulfinyl group, an arylsulfinyl group, an alkoxycarbonyl group, an aryloxycarbonyl group, a carbamoyl group, a thiocarbamoyl group, a carboxyl group, an acyl group, a formyl group, a nitro group, a cyano group and so on, preferably a halogeno-alkyl group (preferably, an alkyl group substituted by halogen at 1-position carbon atom, more preferably perhalogeno-alkyl group), an alkyl group, an arylsulfonyl group, a carbamoyl group, an acyl group and so on. Preferable examples of the alkyl group are a $C_{1-6}$ alkyl group such as methyl, ethyl, propyl, etc., preferable examples of the aryl group are $C_{6-14}$ aryl group such as phenyl, etc., preferable examples of the alkoxy group are a $C_{1-6}$ alkoxy group such as methoxy, ethoxy, etc, and preferable examples of the acyl group are ($C_{1-6}$ alkyl)carbonyl group such as acetyl, ethyl carbonyl, etc.

1 or not less than 2 (preferably 1 to 4) electron-attractive group(s) may be on W, and preferably the sum of Hammet's substituent constant σ (L. P. Hammet, Physical Organic Chemistry, Vol. 2, McGrow-Hill, New York, 1970) of all substituents other than a group represented by the formula: $SO_2X$ is not less than about 0.35.

Examples of the "substituents" and "aromatic ring" of "aromatic ring which may be further substituted" are same those as "substituents" and "aromatic ring" of "aromatic ring which may be substituted" represented by W in case the Z is an electron-attractive group.

The substituents represented by R is not limited so long as the purpose of the present invention can be achieved. Examples of the substituents are a lower alkyl group (preferably $C_{1-6}$ alkyl group) such as methyl, ethyl, propyl, isopropyl, etc.

The aromatic ring represented by Ar and Ar' is not limited so long as the purpose of the present invention can be achieved. Examples of the aromatic ring are the above-mentioned aromatic ring represented by W, benzazepine, benzodiazepine, benzoxazepine, benzothiepine, benzothiazepine, phenothiazine, chroman, isochroman and so on. Preferable examples of the aromatic ring are benzene, thiophene, pyridine, thiazole, etc., and more preferable examples are benzene, etc.

The method of production of the present invention is characterised in that Ar and Ar', respectively, is an aromatic ring. Therefore, the kinds and number of the substituents for the aromatic ring are not limited. Examples of the substituents are the above-mentioned substituents for the aromatic ring represented by W; a $C_{6-14}$ aryl group such as phenyl, naphthyl, anthryl, phenanthryl, acenaphthenyl, etc.; a $C_{6-14}$ cyclic hydrocarbon group such as cyclopropyl, cyclohexyl, etc.; a 5- or 6-membered monocyclic heterocyclic group such as furyl, thienyl, pyrrolyl, oxazolyl, isoxazolyl, thiazolyl, isothiazolyl, imidazolyl, pyrazolyl, pyridyl, pyridazinyl, pyrimidinyl, pyrazinyl, triazinyl, etc. or a hydrogenated monocyclic heterocyclic group thereof; a 8- to 14-membered aromatic condensed heterocyclic group such as benzofuranyl, isobenzofuranyl, benzothienyl, indolyl, isoindolyl, 1H-indazolyl, benzimidazolyl, benzoxazolyl, 1,2-benzoxazolyl, benzothiazolyl, benzopyranyl, quinolyl, isoquinolyl, cinnolinyl, quinazolyl, quinoxalinyl, phthalazinyl, naphthyridinyl, purinyl, pteridinyl, carbazolyl, α-carbolinyl, β-carbolinyl, γ-carbolinyl, acridinyl, phenothiazinyl, phenazinyl, phenoxthinyl, thianthrenyl, phenanthridinyl, phenanthrolinyl, etc. or a hydrogenated condensed heterocyclic group thereof; carboxyl; sulfo; alkyloxycarbonyl; aryloxycarbonyl; alkylcarbamoyl; arylcarbamoyl; alkylamidino; arylamidino; acylamidino; alkylguanidino; arylguanidino; acylguanidino; alkylsulfonyl; arylsulfonyl; alkylsulfamoyl; arylsulfamoyl; alkylsulfinyl; arylsulfinyl; alkoxycarbonyl; aryloxycarbonyl; thiocarbamoyl; carboxyl; acyl; formyl; nitro; cyano; acyloxy; amino; acylamino; mono- or di-alkylamino: mercapto; and so on. The number of the substituents is not limited so long as the substituents can substitute, preferably 1 to 5. Preferable examples of the alkyl group are a $C_{1-6}$ alkyl group such as methyl, ethyl, propyl, etc., preferable examples of the aryl group are $C_{6-14}$ aryl group such as phenyl, etc., preferable examples of the alkoxy group are a $C_{1-6}$ alkoxy group such as methoxy, ethoxy, etc, and preferable examples of the acyl group are ($C_{1-6}$ alkyl)carbonyl group such as acetyl, ethyl carbonyl, etc.

Of the above-mentioned substituents, preferable examples are an amino group, a ($C_{1-6}$ alkoxy)carbonyl amino group such as t-butoxycarbonyl amino, a $C_{7-15}$ aralkyl amino group such as benzyl, an amino group having a 5- or 6-membered heterocycle substituted by $C_{1-6}$ alkyl such as 2-thienylmethyl amino, 2-imidazolylmethyl amino, a group represented by the formula:

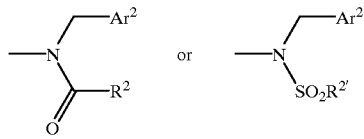

wherein $Ar^2$ is a $C_{6-14}$ aryl group (e.g. phenyl) or a 5- or 6-membered heterocyclic group (e.g. pyridyl, thienyl, imidazolyl), and these groups may be substituted by a $C_{1-6}$ alkoxy group (e.g. methoxy) or a $C_{6-14}$ aryloxy group (e.g. phenyloxy) optionally having $C_{1-6}$ alkoxy (e.g. methoxy); $R^2$ is a phenyl group which may be substituted by $C_{1-6}$ alkoxy (e.g. methoxy), a $C_{1-6}$ alkyl group (e.g. methyl, ethyl, propyl, isopropyl) or a 5- or 6-membered heterocyclic group (e.g. pyridyl); and $R^{2'}$ is a $C_{1-6}$ alkyl group (e.g. methyl, ethyl, propyl, isopropyl).

Preferable examples of $Ar^2$ are phenyl, methoxyphenyl, methoxyphenoxyphenyl, pyridyl, thienyl, thiazolyl, etc.

Preferable examples of $R^2$ are trimethoxyphenyl, isopropyl, pyridyl, etc.

Preferable examples of $R^{2'}$ are methyl, etc.

Specific preferable examples of the linker binding carrier for organic synthesis (I) are a linker binding carrier for organic synthesis wherein the carrier represented by

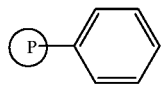

is a carrier represented by

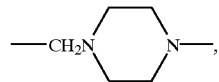

wherein

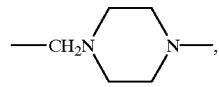

is a polystyrene carrier, X is a halogen atom, Y is a bond, —CH$_2$NH— or a group represented by

—CH$_2$N⟨   ⟩N—,

Z is a sulfonyl group or a carbonyl group, W is a benzene ring, m is 1 or 2, and so on.

And, preferable examples of the linker binding carrier for organic synthesis (II) are a linker binding carrier for organic synthesis wherein X is a chlorine atom, Y is —CH$_2$NH— or a group represented by

—CH$_2$N⟨   ⟩N—,

Z is a sulfonyl group or a carbonyl group and n is 0.

The linker-bound carriers for organic synthesis according to the present invention, their starting materials or synthetic intermediates can be used as salts insofar as they do not interfere with the reaction, and for example, they can be used after conversion into salts with inorganic bases, salts with organic bases, salts with inorganic acids, salts with organic acids, and salts with basic or acidic amino acids.

Preferable examples of salts with inorganic bases include e.g. alkali metal salts such as sodium salt, potassium salt, cesium salt and lithium salt; alkaline earth metal salts such as calcium salt and magnesium salt; and aluminium salt and ammonium salt. Preferable examples of salts with organic bases include salts with organic amines such as, for example, trimethylamine, triethylamine, pyridine, picoline, ethanolamine, diethanolamine, triethanolamine, dicyclohexylamine, N,N'-dibenzyl ethylenediamine and diisopropylamine.

Preferable examples of salts with inorganic acids include salts with for example hydrochloric acid, hydrobromic acid, sulfuric acid, nitric acid and phosphoric acid. Preferable examples of salts with organic acids include salts with for example formic acid, acetic acid, trifluoroacetic acid, fumaric acid, oxalic acid, phthalate, citrate, tartaric acid, maleic acid, citric acid, succinic acid, malic acid, methanesulfonic acid, benzenesulfonic acid, p-toluenesulfonic acid, alkylsulfonic acid or arylsulfonic acid.

Preferable examples of salts with basic amino acids include salts with for example arginine, lysine and ornithine, and preferable examples of salts with acidic amino acids include salts with for example aspartic acid, glutamic acid etc.

BEST MODE FOR CARRYING OUT THE INVENTION

Use of the linker-bound carriers for organic synthesis according to the present invention is advantageous for easily producing many types of compounds having aromatic ring groups (for example, many types of compounds having specific fundamental skeletons including aromatic ring groups having a variety of different substituent groups) simultaneously or in a short period.

Accordingly, the carriers of the present invention can be used to produce many kinds of organic compounds having different substituent groups efficiently in a short time, and these carriers are advantageous in fields such as the field of quantitative analysis and the field of reagent manufacturing where many kinds of compounds having analogous structures are required simultaneously in small amounts, and these carriers are also useful for automation of organic synthesis.

Further, the carriers of this invention can be used as advantageous carriers in "combinatorial chemistry" described in e.g. Chem. Rev., Vol. 97, No. 2, pp. 347–509 (1997), and for example, they are extremely useful for highly efficient synthesis of compounds which can be the subject of evaluation of biological activity targeting agents for treatment of infections, agents for treatment of diseases in the circulatory system, agents for treatment of arteriosclerosis, agents for treatment of diseases in bone and joints, agents for treatment of diseases in the central nervous system, agents for treatment of diabetes, agents for treatment of diseases in the digestive organ system and agents for treatment of allergic diseases. For production of a combinatorial library and for selection of compounds having biological activity therefrom, a method described in Published Unexamined Japanese Application No. 9-504511 or a method conforming thereto is used.

The most distinguishable feature of the linker-bound carriers for organic synthesis according to the present invention is that groups represented by the formula:

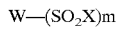

wherein each symbol has the same meaning as defined above, are modified by electron attractive groups.

Compounds represented by the formula:

wherein Ar has the same meaning as defined above, are reacted with the linker-bound carriers for organic synthesis of the present invention having such characteristic, which are represented by the formula:

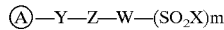 (I)

wherein each symbol has the same meaning as defined above, thereby giving compounds represented by the formula:

 (XX)

wherein each symbol has the same meaning as defined above, which have said aromatic compounds carried as sulfonates on the carriers and which if required may be subjected to necessary synthesis reaction on the carriers, thereby giving compounds represented by the formula:

(XXI)

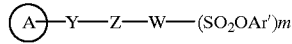

wherein each symbol has the same meaning defined above, and these resulting compounds are reduced whereby the aromatic compounds of the formula:

Ar'—H (XXII)

wherein Ar' has the same meaning as defined above, and the aromatic hydroxy group (i.e. OH on Ar—OH) used for introduction into the carriers has been replaced by a hydrogen atom can be cleaved off from the carriers.

The linker-bound carriers for organic synthesis according to the present invention or salts thereof can be produced by the production method described below or a method conforming thereto.

A. The carrier of the present invention represented by the formula (I) or a salt thereof can be produced by converting the —OH moiety in the group represented by the formula:

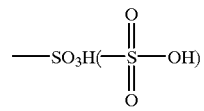

in the compound represented by e.g., the formula:

(XXIII)

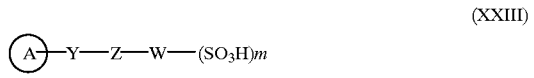

or a salt thereof, into the leaving group X. X has the same meaning as defined above.

Specifically, (1) The carrier (I) wherein X is a halogen atom, or salts thereof, can be obtained by halogenating the compound (XXIII) or a salt thereof.

The compound (XXIII) used or a salt thereof may be one commercially available or one obtained by a method of condensing 3,5-disulfobenzoate onto a carrier having an amino group at the terminal or by a method conforming thereto. Examples of halogenating reagents are sulfuryl halides such as chlorosulfuryl, thionyl halides such as thionyl chloride, halogenosulfonic acids such as chlorosulfonic acid, phosphorus halides such as phosphorus pentachloride, phosphorus oxyhalides such as phosphorus oxychloride. The reaction can be carried out by allowing about 1 to about 10 moles of a halogenating reagent to react with about 1 mole of compound (XXIII) or a salt thereof. This reaction is advantageously conducted in a solvent, and as the solvent, an aprotic solvent such as dichloromethane is used. The reaction is conducted usually for about 0.5 hour to about 72 hours at about −50° C. to about 100° C.

The reaction for halogenation of compound (IV) or salts thereof, or the reaction of compound (XVII) or salts thereof with sulfuryl halide, can be conducted in the same manner as in this method.

(2) By reacting the compound (XXIII) or a salt thereof with an activating reagent for sulfonic acid, it is possible to produce the carrier (I) wherein X is a sulfone group substituted with (i) alkyl or (ii) aryl, or salts thereof.

The activating reagent for sulfonic acid, such as tosyl chloride and mesyl chloride, can be used.

The reaction can be carried out by allowing about 1 to about 10 moles of the activating reagent for sulfonic acid to react with about 1 mole of compound (XXIII) or salts thereof. This reaction is advantageously conducted in a solvent, and as the solvent, an aprotic solvent such as dichloromethane is used. The reaction is conducted usually for about 0.5 hour to about 72 hours at about −50° C. to about 100° C.

Further, the reaction of the compound (IV) or a salt thereof with the activating reagent for sulfonic acid can be carried out in the same manner as in this reaction.

B. (1) By reacting the compound represented by the formula:

  (XXIV)

wherein each symbol has the same meaning as defined above, or a salt thereof with halogenosulfonic acid, it is possible to produce the carrier represented by the formula:

  (XXV)

wherein each symbol has the same meaning as defined above, or a salt thereof, contained in the carrier (I).

The compound (XXIV) or a salt thereof can be produced by applying, to commercial carriers, reaction conditions conventionally used for producing similar compounds in liquid phase reaction. For example, when the carrier is polystyrene, the compound (XXIV) or a salt thereof can be obtained by a method of reacting commercial polystyrene resin with benzene sulfonyl chloride and aluminium chloride or by a method conforming thereto. As the halogenosulfonic acid, chlorosulfonic acid etc. can be used.

The reaction can be carried out by allowing about 1 to about 10 moles of the halogenating reagent to react with about 1 mole of the compound (XXIII) or a salt thereof. This reaction is advantageously conducted in a solvent, and as the solvent, an aprotic solvent such as dichloromethane is used. The reaction is conducted usually for about 0.5 hour to about 72 hours at about −50° C. to about 100° C.

By reacting the compound (VI) or a salt thereof with halogenosulfonic acid in the same manner as in this reaction, it is possible to produce the carrier (VII) or a salt thereof.

C. (1) By reacting the carrier (II) with the compound represented by the formula:

XO₂S—W—(SO₂X)m  (XXVI)

wherein each symbol has the same meaning as defined above, or a salt thereof, it is possible to obtain the carrier represented by the formula:

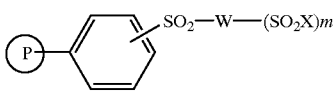  (XXVII)

wherein each symbol has the same meaning as defined above, or a salt thereof contained in carrier (I).

The carrier (II) used in this reaction may be a commercial one, and the compound (XXVI) or a salt thereof may be those commercially available or can be obtained by e.g. a method of reacting its corresponding sulfonic acid with a halogenating reagent such as phosphorus halide (V. V. Kozlov et al., J. Gen. Chem. USSR (Engl. Transl), Vol. 19, p. 740 (1949)).

The reaction can be carried out by allowing about 1 to about 10 moles of the compound (XXVI) and about 1 to about 10 moles of a Lewis acid such as aluminium chloride to react with about 1 mole of the carrier (II) or salts thereof. This reaction is advantageously conducted in a solvent, and as the solvent, an aprotic solvent such as dichloromethane is used. The reaction is completed usually for about 0.5 hour to about 72 hours at about −50° C. to about 100° C.

The method of preparing the carrier (IX) or a salt thereof contained in the carrier (I) by reacting the carrier (II) with the compound (VIII) or a salt thereof can also be carried out in the same manner as in this reaction.

(2) By reacting the carrier (II) with compounds represented by the formula:

XCO—W—(SO₂X)m  (XXVIII)

wherein each symbol has the same meaning as defined above, or a salt thereof, it is possible to obtain the carriers or a salt thereof represented by the formula:

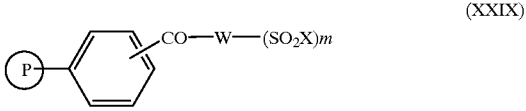  (XXIX)

wherein each symbol has the same meaning as defined above, contained in the carrier (I).

The carrier (II) used in this reaction may be a commercial one, and the compound (XXVIII) or a salt thereof may be one commercially available or can be obtained by e.g. a method of reacting its corresponding carboxylic acid with a halogenating reagent such as phosphorus oxyhalide (D. Binder et al., J. Med. Chem. Vol. 30, p. 678 (1987)).

The reaction can be carried out by allowing about 1 to about 10 moles of the compound (XXVIII) and about 1 to about 10 moles of a Lewis acid such as aluminum chloride to react with about 1 mole of the carrier (II) or a salt thereof. This reaction is advantageously conducted in a solvent, and as the solvent, an aprotic solvent such as dichloromethane is used. The reaction is conducted usually for about 0.5 hour to about 72 hours at about −50° C. to about 100° C.

D. (1) By reacting the compound (X) or a salt thereof with the compound (XXVI) or a salt thereof, it is possible to obtain the carrier represented by the formula:

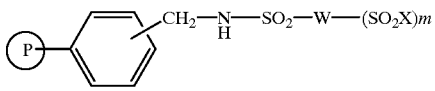

(XXX)

wherein each symbol has the same meaning as defined above, or a salt thereof, contained in the carrier (I).

The carrier (X) used in this reaction may be a commercial one or can be obtained by e.g. a method of reacting commercial Merrifield resin with phthalimide and then reacting the obtained compound with hydrazine, and the compound (XXVI) or a salt thereof may be one commercially available or can be obtained by the method described above.

The reaction can be carried out by allowing about 1 to about 10 moles of the compound (XXVI) and about 1 to about 10 moles of a base such as diisopropyl ethylamine and triethylamine to react with about 1 mole of the carrier (X) or a salt thereof. This reaction is advantageously conducted in a solvent, and as the solvent, an aprotic solvent such as dichloromethane and tetrahydrofuran is used. The reaction is conducted usually for about 0.5 hour to about 72 hours at about −50° C. to about 100° C.

The method of preparing the carrier (XI) or a salt thereof contained in carrier (I) by reacting the compound (X) or a salt thereof with the compound (VIII) or a salt thereof can also be carried out in the same manner as in this reaction.

(2) By reacting the compound (X) or a salt thereof with the compound (XXVIII) or a salt thereof, it is possible to obtain the carrier represented by the formula:

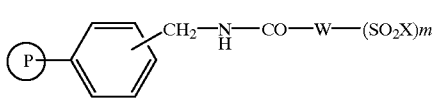

(XXXI)

wherein each symbol has the same meaning as defined above, or a salt thereof contained in the carrier (I).

The carrier (X) used in this reaction may be commercial one or can be obtained by e.g. a method of reacting commercial Merrifield resin with phthalimide and then reacting the obtained compound with hydrazine, and the compound (XXVIII) or a salt thereof may be one commercially available or can be obtained by the method described above.

The reaction can be carried out by allowing about 1 to about 10 moles of the compound (XXVIII) and about 1 to about 10 moles of a base such as diisopropyl ethylamine and triethylamine to react with about 1 mole of the carrier (X) or a salt thereof. This reaction is advantageously conducted in a solvent, and as the solvent, an aprotic solvent such as dichloromethane and tetrahydrofuran is used. The reaction is conducted usually for about 0.5 hour to about 72 hours at about −50° C. to about 100° C.

The method of preparing the carrier (XIII) or a salt thereof contained in the carrier (I) by reacting the compound (X) or a salt thereof with the compound (XII) or a salt thereof can also be carried out in the same manner as in this reaction.

E. (1) By reacting the compound (XIV) or a salt thereof with the compound (XXVI) or a salt thereof, it is possible to obtain the carrier represented by the formula:

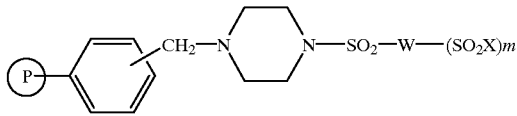

(XXXII)

wherein each symbol has the same meaning as defined above, or a salt thereof contained in the carrier (I).

The carrier (XIV) used in this reaction may be commercial one or can be obtained by e.g. a method of reacting commercial Merrifield resin with piperidine, and the compound (XXVI) or a salt thereof may be one commercially available or can be obtained by the method described above.

The reaction can be carried out by allowing about 1 to about 10 moles of the compound (XXVI) and about 1 to about 10 moles of a base such as diisopropyl ethylamine and triethylamine to react with about 1 mole of the carrier (XIV) or a salt thereof. This reaction is advantageously conducted in a solvent, and as the solvent, an aprotic solvent such as dichloromethane and tetrahydrofuran is used. The reaction is conducted usually for about 0.5 hour to about 72 hours at about −50° C. to about 100° C.

The method of preparing the carrier (XV) or a salt thereof contained in the carrier (I) by reacting the compound (XIV) or a salt thereof with the compound (VIII) or a salt thereof can also be carried out in the same manner as in this reaction.

(2) By reacting the compound (XIV) or a salt thereof with the compound (XXVIII) or a salt thereof, it is possible to obtain the carrier represented by the formula:

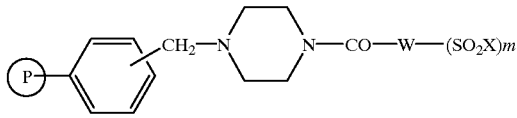

(XXXIII)

wherein each symbol has the same meaning as defined above, or a salt thereof contained in the carrier (I).

The carrier (XIV) used in this reaction may be a commercial one or can be obtained by e.g. a method of reacting commercial Merrifield resin with piperazine, and the compound (XXVIII) or a salt thereof may be one commercially available or can be obtained by the method described above.

The reaction can be carried out by allowing about 1 to about 10 moles of the compound (XXVIII) and about 1 to about 10 moles of a base such as diisopropyl ethylamine and triethylamine to react with about 1 mole of the carrier (XIV) or a salt thereof. This reaction is advantageously conducted in a solvent, and as the solvent, an aprotic solvent such as dichloromethane and tetrahydrofuran is used. The reaction is completed usually for about 0.5 hour to about 72 hours at about −50° C. to about 100° C.

The method of preparing the carrier (XVI) or a salt thereof contained in the carrier (I) by reacting the compound (XIV) or a salt thereof with the compound (XII) or a salt thereof can also be carried out in the same manner as in this reaction.

The desired linker-bound carrier (I) for organic synthesis obtained in this manner, or a salt thereof, can be isolated and purified by e.g. filtration, washing and centrifugation, and when the carrier (I) is obtained as a free form, it is converted into a salt thereof in a usual manner, or when the carrier (I) is obtained as a salt, it is converted into a free from or another salt, and then the carrier can be isolated and purified. Alternatively, the reaction mixture can be used directly as the starting material in the subsequent step.

Hereinafter, a specific example of the process for producing the carrier (I) of the present invention or a salt thereof is described. Here, an example of using polystyrene resin as the carrier is described for the sake of convenience, but this is not intended to limit the present invention, and production from other carriers can also be conducted in the same manner.

a) Method of Converting Sulfonate Resin into Halogenosulfonyl Resin

Resin having a halogenosulfonyl group at the terminal can be obtained by reacting resin having a sulfonate group, which is commercially available or produced in a known method and represented by the formula:

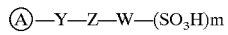

wherein each symbol has the meaning as defined above, with sulfuryl halide and tri-substituted phosphine (e.g. triphenyl phosphine). This reaction is advantageously conducted usually in an aprotic solvent such as dichloromethane and completed for about 0.5 hour to about 24 hours at about −50° C. to about 50° C., preferably at about 0° C. to about 25° C.

b) Method of Producing Resin Having a Halogenosulfonyl Phenyl Group by Reacting a Phenyl Group Which may be Substituted on Resin with a Halogenosulfonic Acid Resin having a halogenosulfonyl phenyl group can be produced by reacting resin such polystyrene resin etc. having a phenyl group which may be substituted, with a halogenosulfonic acid. This reaction is usually conducted for about 1 hour to about 24 hours at about 0° C. to about 150° C., preferably at about 70° C. to about 110° C. in the absence of a solvent or in an inert solvent such as dichloromethane.

c) Method of Producing Resin Having a Halogenosulfonyl Group by Reacting a 1,3-benzenesulfonyl Dihalide Derivative with an Amino Group on Resin Resin having a halogenosulfonyl group is produced by reacting resin having a primary or secondary amino group, such as aminomethyl polystyrene or piperadinomethyl polystyrene with a 1,3-benzene disulfonyl dihalide derivative. This reaction is conducted usually for about 0.5 hour to about 24 hours at about −50° C. to about 50° C., preferably at about 0° C. to about 25° C., in an inert solvent such as dichloromethane or tetrahydrofuran in the coexistence of a base such as diisopropyl ethylamine.

d) Method of Producing Resin Having a Halogenosulfonyl Group by Reacting Polystyrene Resin with a 1,3-benzenesulfonyl Dichloride Derivative This reaction is conducted usually for about 1 hour to about 24 hours at about −50° C. to about 100° C., preferably at about 0° C. to about 25° C., in an inert solvent such as dichloromethane, 1,2-dichloroethane or nitroethane in the presence of a Lewis acid catalyst such as aluminum chloride.

e) Method of Producing Resin Having a Halogenosulfonyl Group by Reacting a 3,5-bis(halogenosulfonyl)benzoyl Halide Derivative with an Amino Group on Resin Resin having a halogenosulfonyl group is produced by reacting resin having a primary or secondary amino group, such as aminomethyl polystyrene or piperadinomethyl polystyrene with a 3,5-bis(halogenosulfonyl)benzoyl halide derivative. This reaction is conducted usually for about 0.5 hour to about 24 hours at about −50° C. to about 50° C., preferably at about 0° C. to about 25° C., in an inert solvent such as dichloromethane or tetrahydrofuran in the coexistence of a base such as diisopropyl ethylamine.

The linker-bound carrier (I) of the present invention or a salt thereof obtained in this manner is extremely useful for rapidly producing many kinds of organic compounds having analogous chemical structures, particularly compounds which may have functional groups unstable to base. Hereinafter, a typical example of its production is illustrated.

Step 1. Loading of a Compound Having an Aromatic Hydroxy Group onto the Linker-bound Carrier (I) for Organic Synthesis A compound having an aromatic hydroxy group, represented by the formula: Ar—OH wherein Ar has the same meaning as defined above, is reacted with and carried onto the linker-bound carrier (I) or salts thereof obtained in the method described above, whereby a compound represented by the formula:

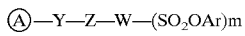

wherein each symbol has the same meaning as defined above, or a salt thereof, can be obtained.

Here, the salts of the compounds represented by the above formula may be any salts which do not interfere with the reaction, and mention can be made of e.g. salts with inorganic bases, salts with organic bases, salts with inorganic acids, salts with organic acids, and salts with basic or acidic amino acids.

Preferable examples of salts with inorganic bases include e.g. alkali metal salts such as sodium salt, potassium salt, lithium salt and cesium salt; alkaline earth metal salts such as calcium salt and magnesium salt; and aluminum salt and ammonium salt. Preferable examples of salts with organic bases include salts with organic amines such as, for example, trimethylamine, triethylamine, pyridine, picoline, ethanolamine, diethanolamine, triethanolamine, dicyclohexylamine, N,N'-dibenzyl ethylenediamine and diisopropylamine.

Preferable examples of salts with inorganic acids include salts with for example hydrochloric acid, hydrobromic acid, sulfuric acid, nitric acid and phosphoric acid. Preferable examples of salts with organic acids include salts with for example formic acid, acetic acid, trifluoroacetic acid, fumaric acid, oxalic acid, phthalate, citrate, tartaric acid, maleic acid, citric acid, succinic acid, malic acid, methanesulfonic acid, benzenesulfonic acid, p-toluenesulfonic acid, alkylsulfonic acid or arylsulfonic acid.

Preferable examples of salts with basic amino acids include salts with for example arginine, lysine and ornithine, and preferable examples of salts with acidic amino acids include salts with for example aspartic acid, glutamic acid etc.

This reaction is conducted usually in the presence of a base, and as the bases, organic amines such as triethylamine, diisopropyl ethylamine and pyridine, metal hydrides such as sodium hydride, metal alkoxides such as t-butoxy potassium and carbonates such as potassium carbonate are preferably used. As the reaction solvent, it is possible to use an organic solvent which is capable of swelling said resin and is inert under the reaction conditions, and tetrahydrofuran, dichloromethane etc. are preferably used. The reaction is conducted usually for about 1 hour to about 24 hours at about −50° C. to about 50° C., preferably about 0° C. to about 25° C. After reaction, excess substrate (the compound having an aromatic hydroxy group) and the base, as well as salts formed during the reaction, can be removed usually by washing them with a suitable solvent.

Step 2. Introduction of a Substituent Group onto Ar in the Above Compound or its Salt and/or Conversion of a Substituent Group on Ar into Another Substituent Group By applying various organic synthesis reactions as necessary, substituent groups can be introduced into Ar on the compound obtained in the step 1 described above, or on salts thereof, and/or the substituent groups on Ar can be converted into other substituent groups. In general, the linker-bound carrier (I) for organic synthesis according to the present invention is chemically stable and can be resistant to various organic conditions such as acidic, basic, oxidative, reductive, heating etc., so a wide variety of reactions can be used insofar as the reaction conditions under which the carrier is not cleaved. The reaction conditions under which the carrier is stable can be easily estimated from the stability of aryl methane sulfonate and aryl toluene sulfonate described for example by T. W. Green and P. G. M. Wuts, Protective Groups in Organic Synthesis, 2nd ed., John Wely & Sons Inc., New York (1991). After the desired reaction is conducted, excess reagents and byproducts derived from the reagents can be removed by washing them with a suitable solvent or by distilling them off under reduced pressure.

Step 3. Cleavage of the Resulting Compound or Salt Thereof

The O—Ar' bond in the aromatic sulfonate is cleaved reductively by reacting the compound obtained in step 2, represented by the formula:

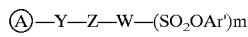

Ⓐ—Y—Z—W—(SO$_2$OAr')m wherein each symbol has the same meaning as defined above, or a salt thereof with a reducing agent, whereby the compound represented by formula: H—Ar' wherein the symbol has the same meaning as defined above, can be obtained. As the reducing agent, a reagent capable of reductively cleaving aryl sulfonates described for example by M. Hudlicky in Reductions in Organic Chemistry, p. 90, John Wely & Sons Inc., New York (1984) can be used, but a combination of a homogeneous system transition metal complex catalyst and a hydride source is preferably used. As the homogenous transition metal complex catalyst, a palladium complex, nickel complex etc. are used preferably. As the hydride source, various formates, various tin (IV) hydrides, various silyl hydrides, and various alkali borohydrides etc. are preferably used, and more preferably, salts of formic acid with organic amines which are easily removed by distillation, or triethylsilane etc. are used.

The aromatic compound represented by the formula: H—Ar' wherein Ar' has the same meaning as defined above, or a salt thereof, which are cleaved off by these treatments, may be purified by conventional purification techniques such as silica gel column chromatography, distillation, sublimation, recrystallization etc. They can be isolated and purified after conversion into salts thereof in a usual manner when H—Ar' is obtained as a free form, or after conversion into a free form or another salt when H—Ar' is obtained as a salt.

In each step for synthesizing the linker-bound carrier for organic synthesis, represented by the formula (I), or a salt thereof and for synthesizing the compounds represented by the formula: Ar'—H wherein Ar' has the same meaning as defined above, protective groups are used when presented as a functional group of NH$_2$, OH, COOH etc. and removed if necessary after the reaction.

If there are functional groups such as protected amino group, protected hydroxy group and protected carboxyl group on Ar—OH, their protective groups may be removed on the carrier, or after cleavage from the carrier, their protective groups may be removed.

The above steps are conducted by using this carrier whereby various organic compounds having aromatic rings can be synthesized. In particular, the carrier is suitable for techniques called combinatorial chemistry in which many kinds of compounds are simultaneously synthesized, and in this case, the carrier can be applied to either the split-mix method and parallel method.

MODES OF WORKING THE INVENTION

Hereinafter, the present invention is described in more detail by reference to Reference Examples, Examples and Comparative Examples, which however are not intended to limit the present invention.

The meanings of abbreviations used in the description are as follows:

Boc: t-butoxycarbonyl
THF: tetrahydrofuran
HOBt: 1-hydroxybenzotriazole
DMF: dimethylformamide
DPPP: 1,3-bis(diphenylphosphino)propane
TFA: trifluoroacetic acid

REFERENCE EXAMPLE 1

Production of N-Boc-aminophenol

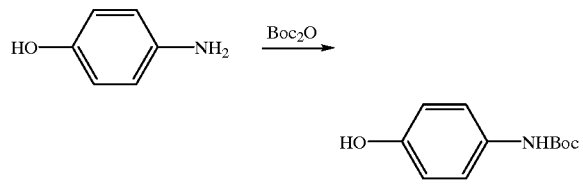

p-Aminophenol (10.9 g, 0.1 mol) was suspended in dry THF (100 ml), and di-t-butyl dicarbonate (23 ml, 0.12 mol) was added thereto, and the mixture was stirred at room temperature overnight. The residue obtained by concentration under reduced pressure was purified by silica gel column chromatography (200 g, ethyl acetate) and recrystallized from ethyl acetate-hexane whereby the title compound, 20.47 g, was obtained as pale yellow crystals.

IR (KBr) 1693 cm$^{-1}$; $^1$H-NMR (CDCl$_3$) d 1.51 (3H, s), 4.86 (1H, s), 6.33 (1H, brs), 6.7–6.8 (2H, m), 7.2–7.3 (2H, m).

REFERENCE EXAMPLE 2

Production of Phenylsulfonyl Resin

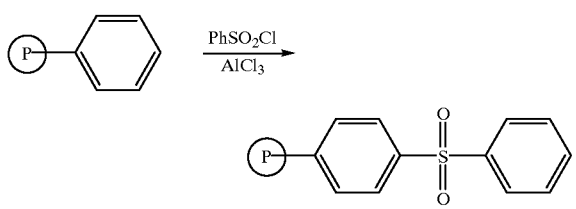

Polystyrene resin (1% DVB, 100–200 mesh, 5 g) was swollen in dry dichloromethane, and benzene sulfonyl chloride (6.4 ml, 0.50 mmol) and aluminium chloride (6.7 g, 50 mmol) were added thereto, and the mixture was stirred at room temperature for 16 hours. THF (50 ml) was added thereto, and the resin was filtered off and washed with THF, 1 N hydrochloric acid-THF (1:1), THF, and diethyl ether in this order and dried in vacuo whereby the title resin, 9.64 g, was obtained.

Anal. S, 10.70.

REFERENCE EXAMPLE 3

Production of Piperazine-1-yl Methyl Resin

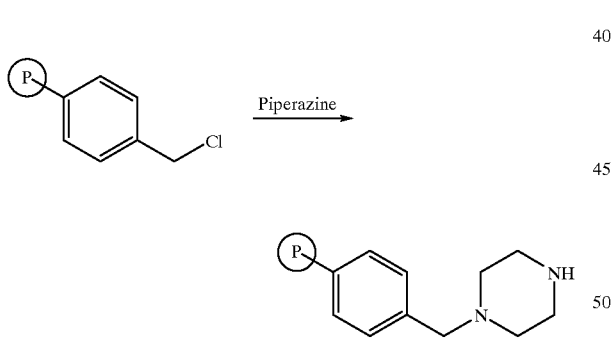

Chloromethyl polystyrene resin (Merrifield resin) (20 g) was swollen in dry dioxane (200 ml), and piperazine (10.3 g, 0.12 mol) was added thereto, and the mixture was stirred at 70° C. for 16 hours. The resin was filtered off and washed with THF, 1 N NaOH-THF, water, THF, and diethyl ether in this order and dried in vacuo whereby the title resin, 20.1 g, was obtained.

Anal. N, 2.65.

REFERENCE EXAMPLE 4

Production of Diphenyl 1,3-benzene Disulfonate

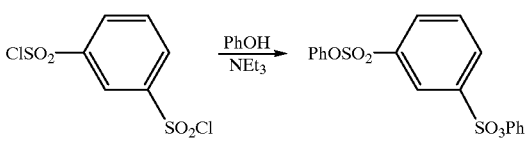

Triethylamine (28 ml, 0.2 mol) was added to a solution of phenol (19 g, 0.2 mol) in dry THF (200 ml), and 1,3-benzene disulfonyl dichloride (25 g, 91 mmol) was added thereto under cooling on ice, and the mixture was stirred at room temperature for 3 hours. 0.5 N hydrochloric acid (200 ml) was added thereto, and the product was extracted with ethyl acetate. The extract was washed with water, saturated aqueous sodium hydrogen carbonate and saturated saline in this order and then dried over magnesium sulfate anhydride. The solvent was distilled off under reduced pressure, and the resulting residue was recrystallized from ethyl acetate-hexane whereby the title compound, 35.5 g, was obtained in colorless crystals.

IR (KBr) 1589, 1484, 1380 cm$^{-1}$; $^1$H-NMR (CDCl$_3$) d 6.9–7.0 (4H, m), 7.2–7.4 (6H, m), 7.71 (1H, t, J=8.0 Hz), 8.10 (2H, dd, J=1.8 and 8.0 Hz), 8.3–8.4 (1H, m).

REFERENCE EXAMPLE 5

Production of 3-(phenoxysulfonyl) Phenylsulfonyl Resin

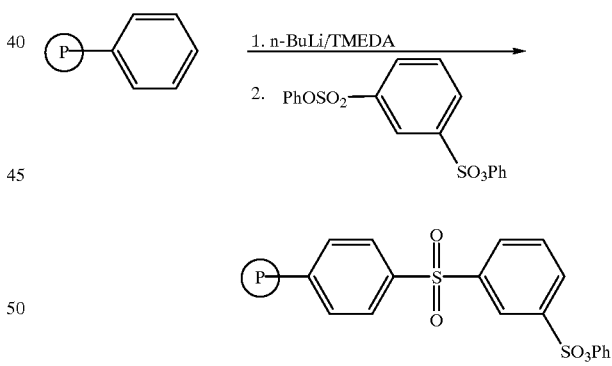

Polystyrene resin (1% DVB, 100–200 mesh, 6 g) was swollen in dry cyclohexane (30 ml), and TMEDA (10 ml, 66 mmol) and 1.6 M n-butyl lithium solution in hexane (50 ml, 80 mmol) were added thereto, and the mixture was stirred at 65° C. for 4.5 hours. The supernatant was removed by decantation, and the resin was washed with dry cyclohexane and then with dry toluene. The resulting resin was swollen in dry toluene (80 ml), and diphenyl 1,3-benzene disulfonate (9.37 g, 24 mmol) was added thereto, and the mixture was stirred at 50° C. overnight. 1 N hydrochloric acid (50 ml) was added thereto, and the resin was filtered off and then washed with THF, 1 N hydrochloric acid-THF (1:1), THF, and diethyl ether in this order and dried in vacuo whereby the title resin, 8.67 g, was obtained.

Anal. S, 5.50.

REFERENCE EXAMPLE 6

Production of 3-sulfophenyl Sulfonyl Resin

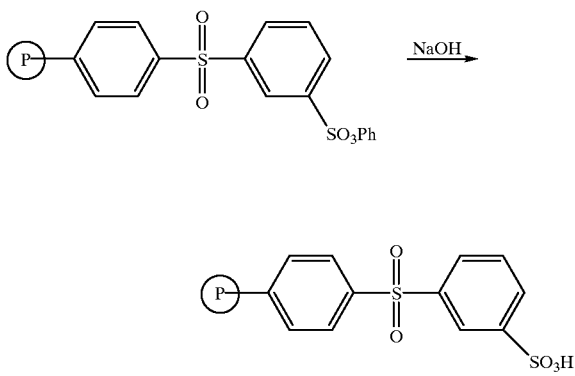

3-(Phenoxysulfonyl)phenyl sulfonyl resin (8.45 g) was swollen in THF (30 ml), and 3 N aqueous sodium hydroxide (15 ml) was added thereto, and the mixture was stirred at 50° C. overnight. The resin was filtered off and washed with water, 1 N hydrochloric acid-THF (1:1), THF, and diethyl ether in this order and dried in vacuo whereby the title resin, 7.60 g, was obtained.

Anal. S, 5.74.

REFERENCE EXAMPLE 7

Production of 3,5-disulfobenzoyl Aminomethyl Resin 2-diisopropyl Ethyl Amine Salt

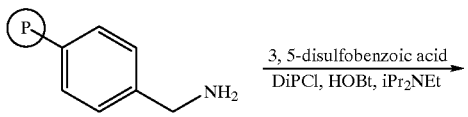

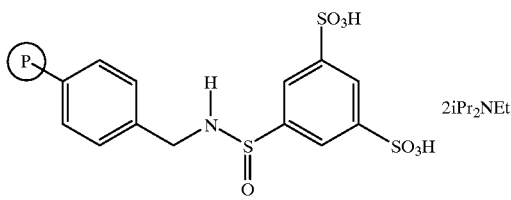

An aqueous solution (300 ml) of disodium 3,5-disulfobenzoate (51.4 g, 157.5 mmol) was adsorbed onto a column packed with sulfonate type ion-exchange resin (HCR-W2, 20–50 mesh, 1 L) and eluted with water. After the resulting eluate was concentrated under reduced pressure, N-methyl pyrrolidone (160 ml), diisopropyl ethylamine (54.9 ml, 315 mmol), and toluene (300 ml) were added thereto, and while water was removed by a Dean-Stark device, the mixture was heated for 12 hours under reflux. The toluene was distilled off under reduced pressure, followed by adding dry N-methyl pyrrolidone (160 ml), HOBt (23.4 g, 173 mmol), aminomethyl resin (1.7 mmol/g, 30 g, 51 mmol), and DIPCI (27.1 ml, 173 mmol) to the resulting residue. The mixture was stirred at room temperature for 4 days. The resin was filtered off and washed with DMF, THF-$H_2O$ (1:1), DMF, methanol, THF, and ether in this order and dried in vacuo whereby the title resin, 59. 22 g, was obtained.

Anal. N, 3.72, S, 5.64.

EXAMPLE 1

Production of 3-(chlorosulfonyl)phenyl Sulfonyl Resin

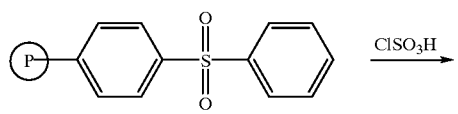

Chlorosulfonic acid (80 ml) was added to the phenyl sulfonyl resin (8.43 g) obtained in the method of Reference Example 2, and the mixture was stirred at 80° C. for 12 hours. The resulting resin was filtered off and then washed with dry dichloromethane, dry THF, and dry diethyl ether in this order and dried in vacuo whereby the title resin, 11.6 g, was obtained.

Anal. S, 15.65, Cl, 8.22.

EXAMPLE 2

Loading of N-Boc-aminophenol onto 3-(chlorosulfonyl)phenyl Sulfonyl Resin

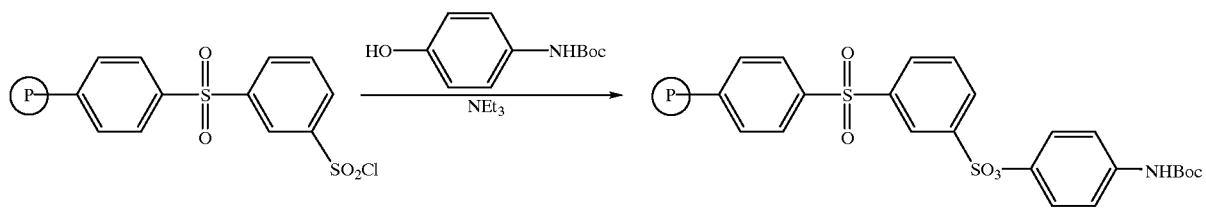

A solution of N-Boc-aminophenol (6.3 g, 30 mmol) and triethylamine (4.2 ml, 30 mmol) in dry THF (30 ml) was added to the 3-(chlorosulfonyl)phenyl sulfonyl resin (3 g) obtained in the method of Example 1, and the mixture was stirred at room temperature for 21 hours. The resulting resin was filtered, then washed with DMF, 1 N hydrochloric acid-THF (1:1), DMF, methanol, THF, and diethyl ether in this order and dried in vacuo whereby the N-Boc-aminophenoxy sulfonyl phenyl sulfonyl resin, 3.59 g, was obtained.

Anal. N, 1.65, S, 13.00.

EXAMPLE 3

Removal of Boc from N-Boc-aminophenoxysulfonyl Phenyl Sulfonyl Resin

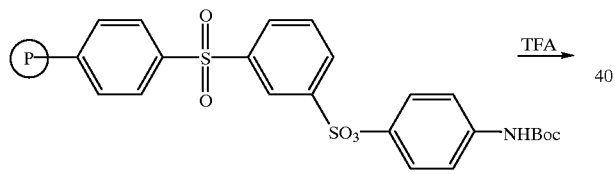

TFA-dichloromethane (1:1, 20 ml) was added to the N-Boc-aminophenoxysulfonyl phenyl sulfonyl resin (3.4 g), and the mixture was stirred at room temperature for 2 hours. The resulting resin was filtered off and then washed with THF, DMF, methanol, THF, and diethyl ether in this order and dried in vacuo whereby the aminophenoxysulfonyl phenyl sulfonyl resin, 3.06 g, was obtained.

Anal. N, 1.75, S, 13.78.

EXAMPLE 4

Production of N-benzylaminophenoxysulfonyl Phenyl Sulfonyl Resin

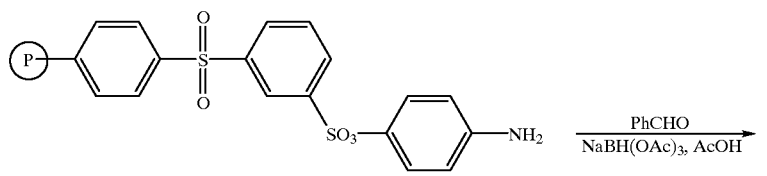

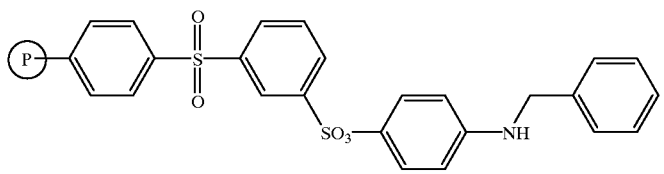

(1) The aminophenoxy sulfonyl phenyl sulfonyl resin (600 mg) was swollen in dichloromethane (2 ml), and benzaldehyde (0.16 ml) was added thereto, and the mixture was stirred at room temperature for 3 hours. Dichloromethane (4 ml) was added to the resulting suspension, and acetic acid (0.22 ml, 3.8 mmol) and sodium triacetoxy borohydride (0.8 g, 3.8 mmol) were added thereto, and the mixture was stirred at room temperature for 18 hours. The resulting resin was filtered and then washed with methanol, DMF, methanol, THF, and diethyl ether in this order and dried in vacuo whereby the title resin, 647 mg, was obtained.

(2) Nicotine aldehyde (b), 2-thiophene carboxy aldehyde (c), 2-formylthiazole (d), p-methoxybenzaldehyde (e), m-methoxybenzaldehyde (f), 4-phenoxybenzaldehyde (g), 3-(4-methoxyphenoxy)benzaldehyde (h) were allowed to act respectively in place of benzaldehyde (a) in the same manner as in (1) above whereby the following corresponding resins were obtained.

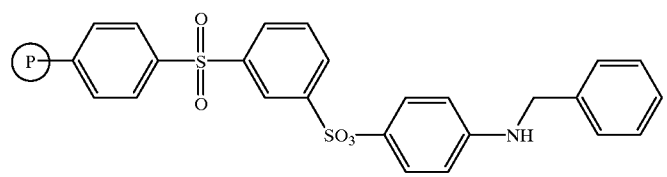

(a)

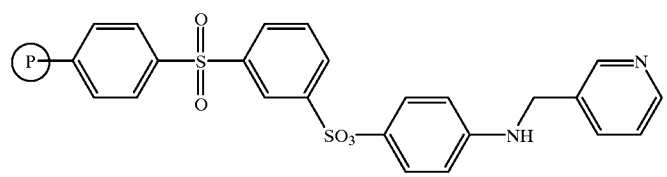

(b)

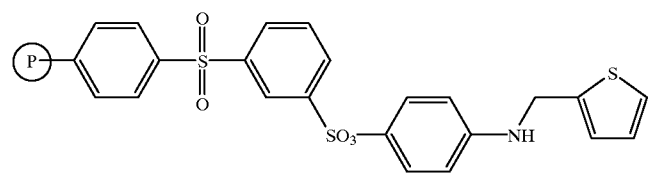

(c)

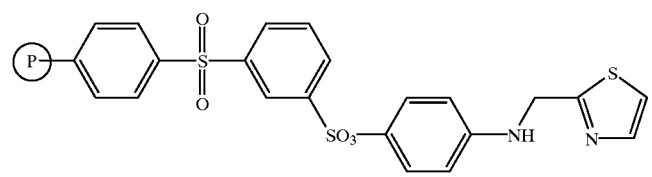

(d)

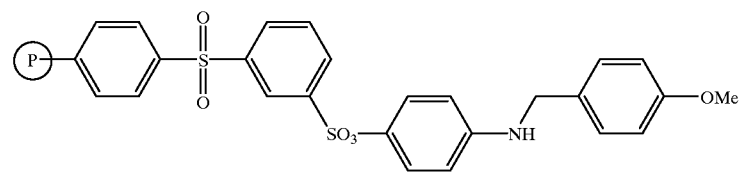

(e)

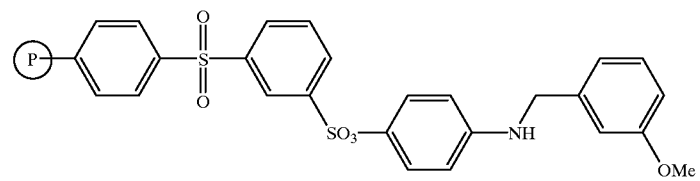

(f)

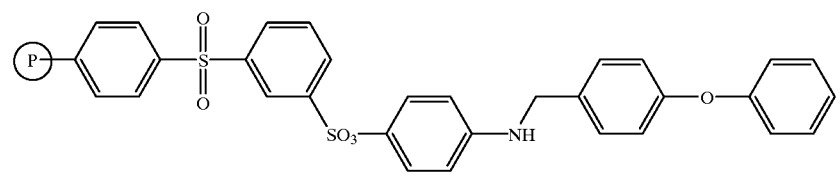

(g)

(h)

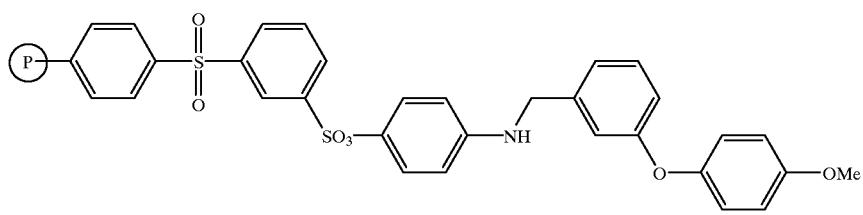

EXAMPLE 5

Production of N-benzyl-N-(3,4,5-trimethoxybenzoyl)-aminophenoxysulfonyl Phenyl Sulfonyl Resin

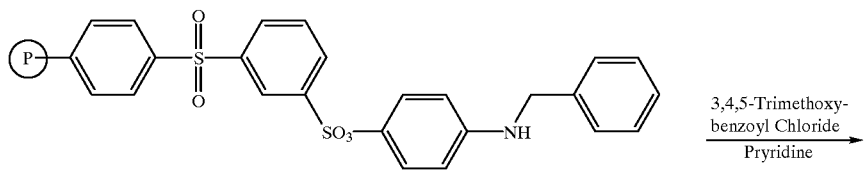

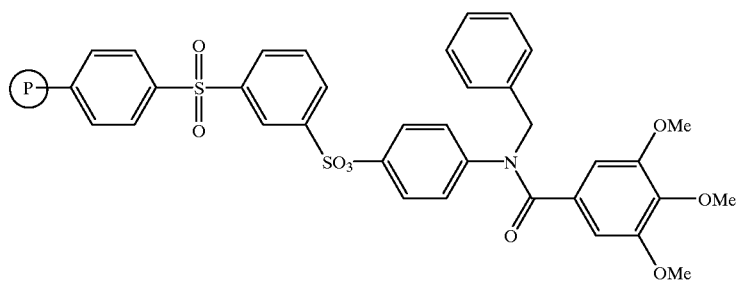

The N-benzylaminophenoxysulfonyl phenyl sulfonyl resin (40 mg) was swollen in dry THF (0.4 ml), and pyridine (0.06 ml, 0.6 mmol) were added thereto, and a solution of 3,4,5-trimethoxybenzoyl chloride (115 mg, 0.5 mmol) in dry THF (0.4 ml) was added thereto, and the mixture was stirred at room temperature for 14 hours. The resulting resin was filtered off and washed with DMF, water-THF (1:1), DMF, methanol, THF, and diethyl ether in this order and dried in vacuo whereby the title resin, 46 mg, was obtained.

EXAMPLE 6

Production of N-benzyl-N-phenyl-3,4,5-trimethoxybenzamide by Reductive Cleavage

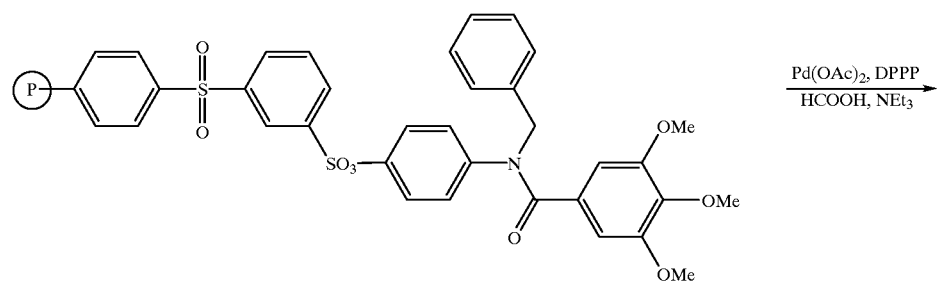

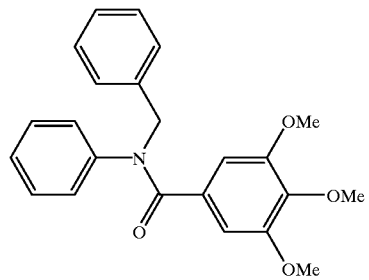

A solution, 0.3 ml, obtained by dissolving palladium acetate (33 mg, 0.15 mmol) and DPPP (69 mg, 0.17 mmol) in dry THF and then adding triethylamine (1.7 ml, 12 mmol) and formic acid (0.45 ml, 12 mmol) thereto was added to the N-benzyl-N-(3,4,5-trimethoxybenzoyl)-aminophenoxysulfonyl phenyl sulfonyl resin (46 mg) and stirred at 90° C. for 12 hours. The resulting resin was filtered off and washed with THF, and the filtrate and the wash were combined and concentrated under reduced pressure. The resulting residue was purified by silica gel chromatography (0.25 g, ethyl acetate) whereby the title compound, 2.7 mg, was obtained.

IR (KBr) 1644 cm$^{-1}$; $^1$H-NMR (CDCl$_3$) d 3.61 (6H, s), 3.78 (3H, s), 5.13 (2H, s), 6.59 (2H, s), 6.9–7.3 (10H, m).

EXAMPLE 7

Production of N-benzyl-N-phenyl-3,4,5-trimethoxybenzamide by Reductive Cleavage

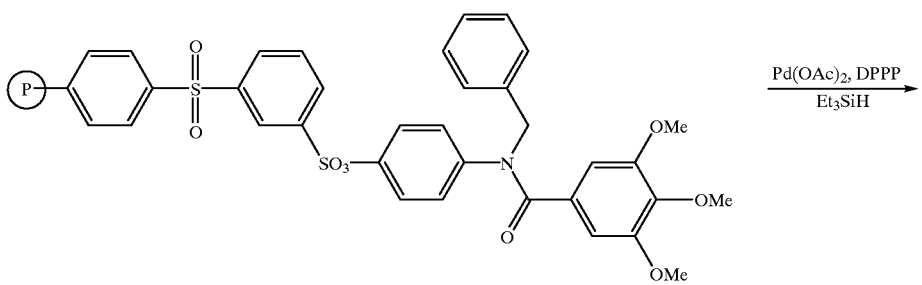

(1) The title compound was obtained in the same manner as in Example 6 except that triethyl silane was used in place of triethylamine and formic acid.

(2) The following compounds were obtained in the same manner as in (1) above.

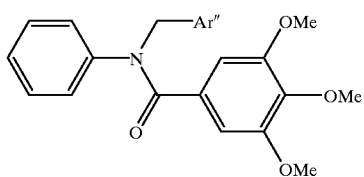
1a-h

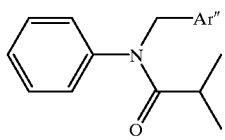
2a-h

-continued

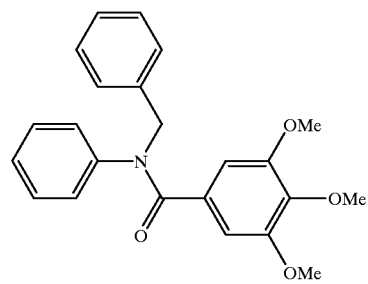

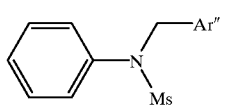
3a-h

39
-continued

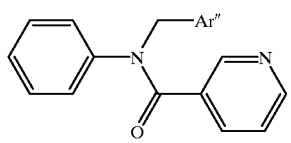
4a-h wherein Ar" represents the following groups.

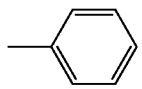
a

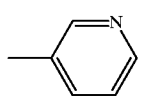
b

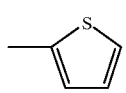
c

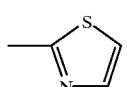
d e

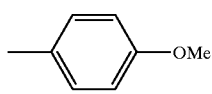
f

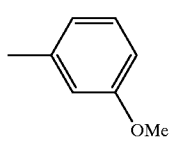

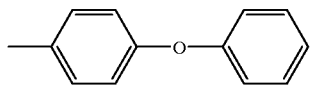
g

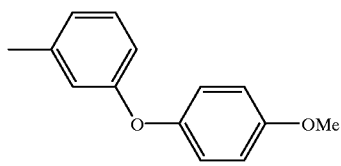
h

1a: 1644 cm$^{-1}$, 1b: 1644 cm$^{-1}$, 1c: 1642 cm$^{-1}$, 1d: 1645 cm$^{-1}$,
1e: 1642 cm$^{-1}$, 1f: 1642 cm$^{-1}$, 1g: 1642 cm$^{-1}$, 1h: 1644 cm$^{-1}$,
2a: 1655 cm$^{-1}$, 2b: 1655 cm$^{-1}$, 2c: 1655 cm$^{-1}$, 2d: 1659 cm$^{-1}$,
2e: 1655 cm$^{-1}$, 2f: 1655 cm$^{-1}$, 2g: 1655 cm$^{-1}$, 2h: 1655 cm$^{-1}$,
3a: 1335 cm$^{-1}$, 3b: 1339 cm$^{-1}$, 3c: 1335 cm$^{-1}$, 3d: 1343 cm$^{-1}$,
3e: 1335 cm$^{-1}$, 3f: 1339 cm$^{-1}$, 3g: 1341 cm$^{-1}$, 3h: 1341 cm$^{-1}$,
4a: 1644 cm$^{-1}$, 4b: 1644 cm$^{-1}$, 4c: 1644 cm$^{-1}$, 4d: 1652 cm$^{-1}$,
4e: 1644 cm$^{-1}$, 4f: 1644 cm$^{-1}$, 4g: 1644 cm$^{-1}$, 4h: 1646 cm$^{-1}$,

40
EXAMPLE 8

Production of 3-(chlorosulfonyl)phenyl Sulfonyl Resin

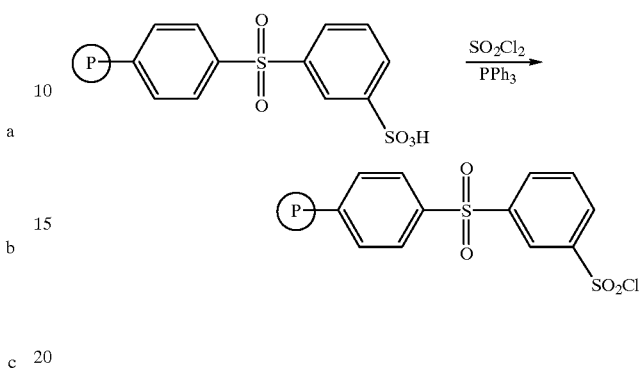

Triphenyl phosphine (10 g, 38 mmol) was dissolved in dry dichloromethane (50 ml), and sulfuryl chloride (3.1 ml, 38 mmol) and the 3-sulfophenyl sulfonyl resin (7.46 g) obtained in the method of Reference Example 6 were successively added thereto under cooling on ice and left at room temperature for 20 hours with occasional shaking. The resulting resin was filtered off, washed with dry dichloromethane and dried in vacuo whereby the title resin, 8.28 g, was obtained.

Anal. S, 4.97.

EXAMPLE 9

Production of 3-(chlorosulfonyl)phenyl Sulfonyl Aminomethyl Resin

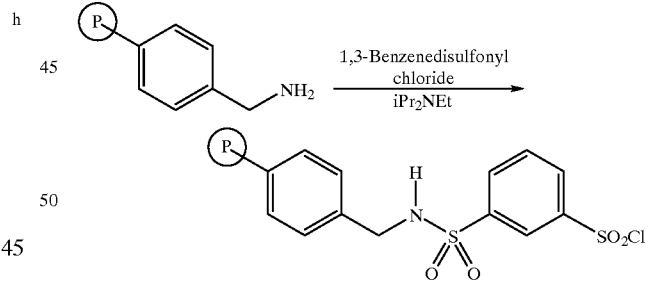

Aminomethyl resin (1 g) was washed with dry THF and then with dry dichloromethane, and dry dichloromethane (10 ml), diisopropyl ethylamine (0.63 ml, 3.6 mmol). and 1,3-benzene disulfonyl chloride (0.99 g, 3.6 mmol) were added thereto in this order and stirred at room temperature for 1 day. The resin was filtered off and washed with 1 N hydrochloric acid-THF, THF, and diethyl ether and dried in vacuo whereby the title resin, 1.40 g, was obtained.

Anal. S, 6.47.

EXAMPLE 10

Production of 4-[3-(chlorosulfonyl)phenyl Sulfonyl]piperazine-1-yl Methyl Resin

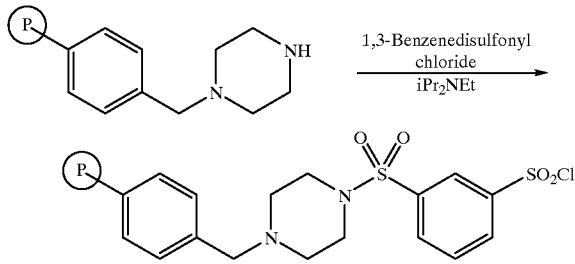

The piperazine-1-yl methyl resin (1 g) obtained in the method of Reference Example 3 was washed with dry THF and then with dry dichloromethane, and dry dichloromethane (10 ml), diisopropyl ethylamine (0.63 ml, 3.6 mmol), and 1,3-benzene disulfonyl chloride (0.99 g, 3.6 mmol) were added thereto in this order and stirred at room temperature for 1 day. The resin was filtered off and washed with 1 N hydrochloric acid-THF, THF, and diethyl ether and dried in vacuo whereby the title resin, 1.26 g, was obtained.

Anal. S, 3.10.

EXAMPLE 11

Production of 3,5-bis(chlorosulfonyl)benzoyl Aminomethyl Resin

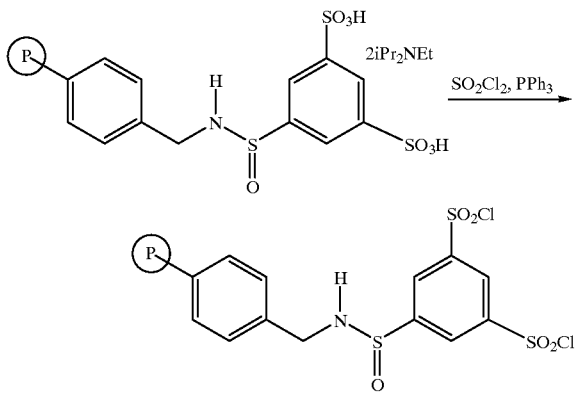

A solution of triphenyl phosphine (23.6 g, 90 mol) in dichloromethane (150 ml) was cooled at −78° C., and sulfuryl chloride (8.0 ml, 100 mmol) and the 3,5-disulfobenzoyl aminomethyl resin 2-diisopropyl ethyl amine salt (10 g) obtained in the method of Reference Example 7 were added thereto, and the mixture was stirred at room temperature for 22 hours. The resulting resin was filtered off and then washed with THF, THF-1 N hydrochloric acid (1:1), THF, and dry ether in this order whereby the title resin, 8.27 g, was obtained.

EXAMPLE 12

Production of 3-(chlorosulfonyl)-2,4,6-trimethylphenyl Sulfonyl Resin

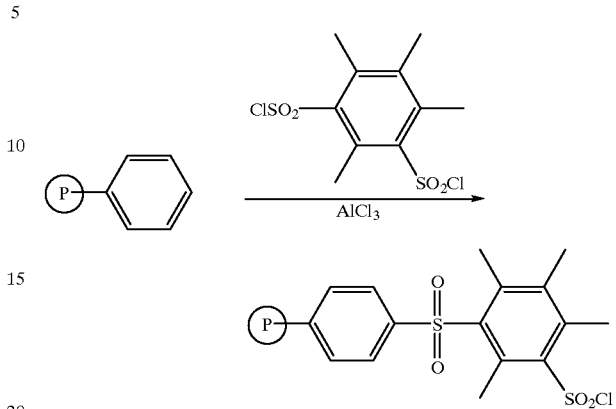

Polystyrene resin (1 g) was swollen in dry dichloromethane (10 ml), and 2,4,5,6-tetramethyl-1,3-benzene disulfonyl dichloride (4 g) and aluminum chloride (1.6 g) were added thereto, and the mixture was stirred at room temperature overnight. The resulting resin was filtered off and then washed with dichloromethane, 1 N hydrochloric acid-THF, THF, and diethyl ether in this order and dried in vacuo whereby the title resin, 2.06 g, was obtained.

Anal. S, 10.34, Cl, 5.47.

COMPARATIVE EXAMPLE 1

(1) Production of Chloro Sulfonyl Resin

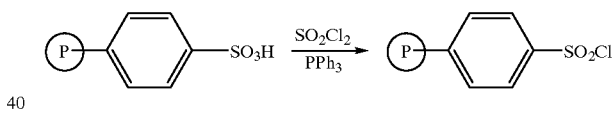

Sulfuryl chloride (16ml) was added to a dichloromethane solution of triphenyl phosphine (47.2 g) at −78° C. and sulfonic acid type-ion exchange resin (Bio-Rad AG50WX2, resin dried over $P_2O_5$, 10 g) was added to the resulting solution. The mixture was stirred at room temperature for 22 hours. The resulting resin was filtered, then washed with dried dichloromethane (50 ml) and dried in vacuo whereby the chloro sulfonyl resin, 11.7 g, was obtained.

(2) Loading of 4-acetamidophenol onto Chloro Sulfonyl Resin

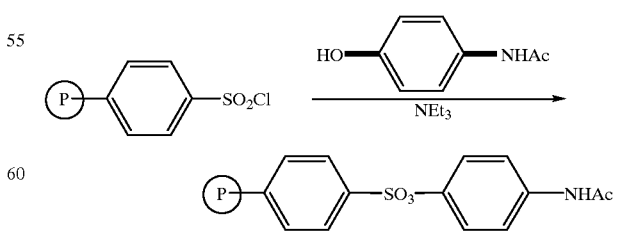

A dried THF (10 ml), 4-acetamidophenol (2.27 g) and triethylamine (2.1 ml) were added to the resin (937 mg) obtained in the above (1), and the mixture was stirred at room temperature for 16 hours. 1 N HCl (20 ml) was added to the reaction solution and the resulting resin was filtered, then washed with DMF, 1 N hydrochloric acid-THF (1:1), DMF, THF, methanol, THF and diethyl ether in this order and dried in vacuo whereby the 4-acetamido phenoxy sulfonyl resin, 1.31 g, was obtained.

(3) Discussion of Reductive Cleavage

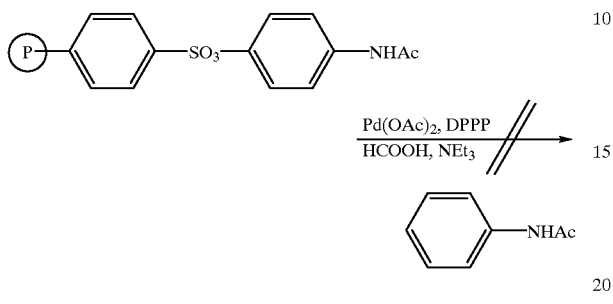

The reaction was conducted by using the resin obtained in the above (2) under the same condition as Example 6. However, acetanilide was not obtained.

INDUSTRIAL APPLICABILITY

By using of the carrier (I) of the present invention, or a salt thereof, many kinds of organic compounds bearing different substituent groups can be produced efficiently in a short time.

What is claimed is:

1. A linker binding carrier for organic synthesis represented by the formula:

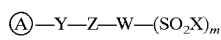

wherein

is a carrier represented by

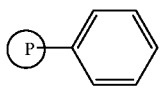

wherein

is a polystyrene carrier,
X is a leaving group which is
  (i) a halogen atom or
  (ii) a sulfonyloxy group substituted by alkyl or aryl,
Y is a bond or spacer selected from the group consisting of

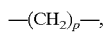     (i)

     (ii)

     (iii)

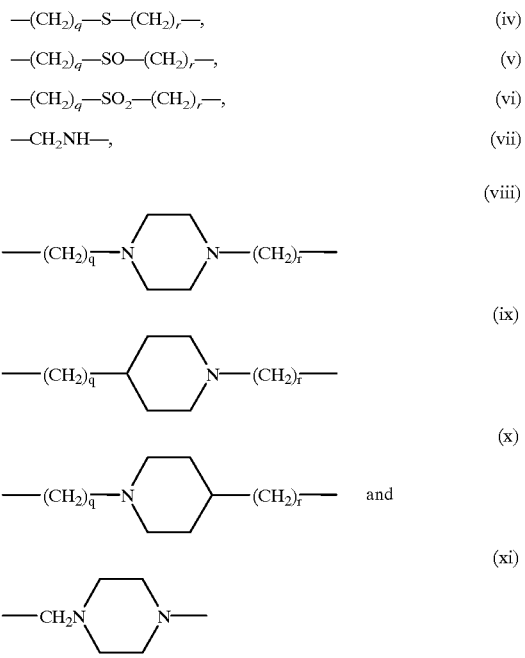

wherein p is an integer of 1 to 6,
  q is an integer of 1 to 3,
  r is an integer of 1 to 3 and
  $R^1$ is a $C_{1-6}$ alkyl group,
Z is a bivalent group such that
when Z is a bivalent electron attractive group,
  the bivalent electron attractive group represented by Z is a carbonyl group, a thiocarbonyl group, a sulfonyl group, a sulfinyl group, a carbamoyl group, a thiocarbamoyl group, a halogeno-methene group or a halogeno-ethene group,
  W is an aromatic ring which may be substituted, wherein the aromatic ring is (i) a $C_{6-14}$ aromatic hydrocarbon or (ii) an aromatic heterocycle containing 1 to 4 hetero atoms selected from the group consisting of an oxygen atom, a sulfur atom and a nitrogen atom or its condensed ring,
  and the $C_{6-14}$ aromatic hydrocarbon and the aromatic heterocycle or its condensed ring may be substituted by
  (i) a halogen atom,
  (ii) a $C_{1-6}$ alkyl group which may be substituted by 1 to 3 halogens,
  (iii) a $C_{1-6}$ alkoxy group which may be substituted by 1 to 3 halogens,
  (iv) a $C_{1-6}$ alkylthio group which may be substituted by 1 to 3 halogens and
  (v) a hydroxy group,
when Z is a bivalent non-electron attractive group,
  the bivalent non-electron attractive group represented by Z is a $C_{1-6}$ alkylene group, $C_{2-6}$ alkenylene group or $C_{2-6}$ alkynylene group, which is substituted by hydroxy, amino, carboxyl, nitro, (mono- or di-$C_{1-6}$ alkyl)amino, $C_{1-6}$ alkoxy, ($C_{1-6}$ alkyl) carbonyloxy or a halogen atom,
  W is an aromatic ring which may be substituted by an electron attractive group and may be further substituted
  wherein the aromatic ring W is (i) a $C_{6-14}$ aromatic hydrocarbon or (ii) an aromatic heterocycle containing 1 to 4 hetero atoms selected from the group consisting of an oxygen atom, a sulfur atom and a nitrogen atom or its condensed ring, and the $C_{6-14}$ aromatic hydrocarbon and the aromatic heterocycle or its condensed ring may be substituted by
(i) a halogen atom,
(ii) a $C_{1-6}$ alkyl group which may be substituted by 1 to 3 halogens,
(iii) a $C_{1-6}$ alkoxy group which may be substituted by 1 to 3 halogens,
(iv) a $C_{1-6}$ alkylthio group which may be substituted by 1 to 3 halogens and
(v) a hydroxy group,
and wherein the electron attractive group substituted on the ring represented by W is a halogen atom, a halogeno-$C_{1-6}$ alkyl group, a halogeno-$C_{6-14}$ aryl group, a $C_{1-6}$ alkylsulfonyl group, a $C_{6-14}$ aryl sulfonyl group, a $C_{1-6}$ alkylsulfamoyl group, a $C_{6-14}$ arylsulfamoyl group, a $C_{1-6}$ alkylsulfinyl group, a $C_{6-14}$ arylsulfinyl group, a $C_{1-6}$ alkoxycarbonyl group, a $C_{6-14}$ aryloxy-carbonyl group, a carbamoyl group, a thiocarbamoyl group, a carboxyl group, an acyl group, a formyl group, a nitro group or a cyano group,
and m is 1 or 2,
or a salt thereof.

2. A linker binding carrier for organic synthesis or a salt thereof as claimed in claim 1, wherein X is
(i) a halogen atom or
(ii) a sulfonyloxy group substituted by $C_{1-6}$ alkyl or $C_{6-14}$ aryl.

3. A linker binding carrier for organic synthesis or a salt thereof as claimed in claim 1, wherein X is a halogen atom.

4. A linker binding carrier for organic synthesis or a salt thereof as claimed in claim 1, wherein X is a chlorine atom.

5. A linker binding carrier for organic synthesis or a salt thereof as claimed in claim 1, wherein the spacer represented by Y is
(i) —(CH$_2$)q—NR$^1$—(CH$_2$)r—, or

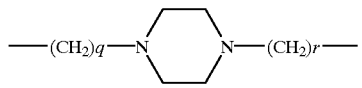

wherein q is an integer of 1 to 3, r is an integer of 1 to 3 and R$^1$ is a $C_{1-6}$ alkyl group.

6. A linker binding carrier for organic synthesis or a salt thereof as claimed in claim 1, wherein Y is a bond, —CH$_2$NH— or a group represented by

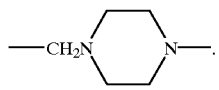

7. A linker binding carrier for organic synthesis or a salt thereof as claimed in claim 1, wherein the bivalent electron attractive group represented by Z is a substituent group wherein the Hammet's substituent constant σ has a positive value.

8. A linker binding carrier for organic synthesis or a salt thereof as claimed in claim 1, wherein the bivalent electron attractive group represented by Z is a carbonyl group, a thiocarbonyl group, a sulfonyl group or a sulfinyl group.

9. A linker binding carrier for organic synthesis or a salt thereof as claimed in claim 1, wherein the bivalent electron attractive group represented by Z is a carbonyl group or a sulfonyl group.

10. A linker binding carrier for organic synthesis or a salt thereof as claimed in claim 1, wherein the bivalent non-electron attractive group represented by Z is a methylene group or an ethylene group.

11. A linker binding carrier for organic synthesis or a salt thereof as claimed in claim 1, wherein Y is a bond and Z is a sulfonyl group or a carbonyl group.

12. A linker binding carrier for organic synthesis or a salt thereof as claimed in claim 1, wherein Y is —CH$_2$NH— or a group represented by

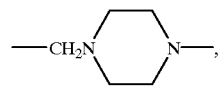

Z is a sulfonyl group or a carbonyl group.

13. A linker binding carrier for organic synthesis or a salt thereof as claimed in claim 1, wherein aromatic ring W is a $C_{6-14}$ aromatic hydrocarbon, and said $C_{6-14}$ aromatic hydrocarbon is a benzene ring.

14. A linker binding carrier for organic synthesis or a salt thereof as claimed in claim 1, wherein aromatic ring W is an aromatic heterocycle, and said aromatic heterocycle or its condensed ring is furan, thiophene, pyrrole, oxazole, isoxazole, thiazole, isothiazole, imidazole, pyrazole, pyridine, pyridazine, pyrimidine, pyrazine, triazine, benzofuran, isobenzofuran, benzothiophene, indole, isoindole, 1H-indazole, benzimidazole, benzoxazole, 1,2-benzisoxazole, benzothiazole, benzopyran, quinoline, isoquinoline, cinnoline, quinazoline, quinoxaline, phthalazine, naphthyridine, purine, pteridine, carbazole, α-carboline, β-carboline, γ-carboline, acridine, phenoxazine, phenothiazine, phenazine, phenoxthin, thianthrene, phenanthridine or phenanthroline.

15. A linker binding carrier for organic synthesis or a salt thereof as claimed in claim 1, wherein the polystyrene carrier is a co-polymer comprising a styrene and 0 to 5 mol % of divinylbenzene thereto.

16. A linker binding carrier for organic synthesis or a salt thereof as claimed in claim 1, which is represented by the formula:

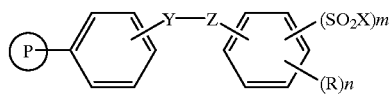

wherein

Ⓟ is a polystyrene carrier, R is a lower alkyl group, n is an integer of 0 to 4 and when n is not less than 2, R may be same or different, the sum of m and n is not more than 5, and other symbols are as defined in claim 1.

17. A linker binding carrier for organic synthesis or a salt thereof as claimed in claim 16, wherein X is a chlorine atom.

18. A linker binding carrier for organic synthesis or a salt thereof as claimed in claim 16, wherein Y is —CH$_2$NH— or a group represented by

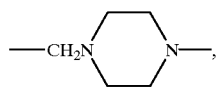

Z is a sulfonyl or carbonyl group and n is 0.

19. A linker binding carrier for organic synthesis or a salt thereof as claimed in claim 1, wherein the carrier represented by

is a carrier represented by

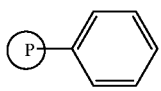

wherein

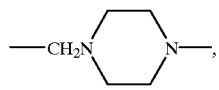

is a polystyrene carrier, X is a halogen atom, Y is a bond, —CH$_2$NH— or a group represented by —CH$_2$N⟨piperazine⟩N—, Z is a sulfonyl group or a carbonyl group, W is a benzene ring, m is 1 or 2.

* * * * *